(12) United States Patent
Lee et al.

(10) Patent No.: US 11,246,615 B2
(45) Date of Patent: Feb. 15, 2022

(54) SURGICAL INSTRUMENT

(71) Applicant: LIVSMED INC., Seongnam-si (KR)

(72) Inventors: Jung Joo Lee, Seoul (KR); Hee Jin Kim, Seoul (KR); Du Jin Bach, Seoul (KR)

(73) Assignee: LIVSMED INC., Seongnam-si (KR)

( * ) Notice: Subject to any disclaimer, the term of this patent is extended or adjusted under 35 U.S.C. 154(b) by 249 days.

(21) Appl. No.: 16/723,378

(22) Filed: Dec. 20, 2019

(65) Prior Publication Data

US 2020/0121345 A1   Apr. 23, 2020

Related U.S. Application Data

(62) Division of application No. 15/306,371, filed as application No. PCT/KR2014/009599 on Oct. 14, 2014, now Pat. No. 10,631,886.

(30) Foreign Application Priority Data

Apr. 24, 2014 (KR) .................. 10-2014-0049460

(51) Int. Cl.
*A61B 17/29* (2006.01)
*A61B 17/00* (2006.01)
*A61B 34/00* (2016.01)

(52) U.S. Cl.
CPC .... *A61B 17/2909* (2013.01); *A61B 17/00234* (2013.01); *A61B 17/29* (2013.01);
(Continued)

(58) Field of Classification Search
CPC .... A61B 2017/2926; A61B 2017/2927; A61B 2017/2932; A61B 2017/2938;
(Continued)

(56) References Cited

U.S. PATENT DOCUMENTS 3,273,408 A   9/1966 Nagel
3,529,481 A   9/1970 Budzyn
(Continued)

FOREIGN PATENT DOCUMENTS

CN   102131469 A   7/2011
JP   S59102587 A   6/1984
(Continued)

*Primary Examiner* — Majid Jamialahmadi
(74) *Attorney, Agent, or Firm* — Novick, Kim & Lee, PLLC; Sang Ho Lee; Hyun Woo Shin

(57) ABSTRACT

Provided is a surgical instrument including: an end tool including a first jaw and a second jaw configured to rotate independently; an operator including a pitch operator controlling a pitch motion of the end tool, a yaw operator controlling a yaw motion of the end tool, and an actuation operator controlling an actuation motion of the end tool; an operating force transmitter including a first jaw wire connected with the first jaw to transmit an operation of the operator to the first jaw, a second jaw wire connected with the second jaw to transmit an operation of the operator to the second jaw, and one or more differential members transmitting a rotation of the yaw operator or the actuation operator to the first jaw or the second jaw via the first jaw wire or the second jaw wire; and a connector configured to extend in a first direction (X axis) and having one end portion coupled to the end tool and the other end portion coupled to the operator to connect the operator and the end tool, wherein the pitch operator is configured to rotate around a second direction (Y axis) perpendicular to the first direction; and at least a portion of the operator is configured to be more adjacent to the end tool than a rotating axis of the operator in at least any one operation state of the operator.

13 Claims, 20 Drawing Sheets

(52) U.S. Cl.
CPC .... *A61B 34/71* (2016.02); *A61B 2017/00323* (2013.01); *A61B 2017/2911* (2013.01); *A61B 2017/2912* (2013.01); *A61B 2017/2923* (2013.01); *A61B 2017/2925* (2013.01); *A61B 2017/2927* (2013.01)

(58) Field of Classification Search
CPC .... A61B 2017/2939; A61B 2017/2912; A61B 34/30; A61B 34/71; A61B 34/70; A61B 2034/305
See application file for complete search history.

(56) References Cited

U.S. PATENT DOCUMENTS

| | | | |
|---|---|---|---|
| 5,478,347 | A | 12/1995 | Aranyi |
| 5,539,987 | A | 7/1996 | Zennyoji |
| 5,792,165 | A | 8/1998 | Klieman et al. |
| 5,797,900 | A | 8/1998 | Madhani et al. |
| 5,908,436 | A | 6/1999 | Cuschieri et al. |
| 5,954,731 | A | 9/1999 | Yoon |
| 6,191,017 | B1 | 2/2001 | Chittipeddi et al. |
| 6,394,998 | B1 | 5/2002 | Wallace et al. |
| 6,432,112 | B2 | 8/2002 | Brock et al. |
| 6,554,844 | B2 | 4/2003 | Lee et al. |
| 6,676,684 | B1 | 1/2004 | Morley et al. |
| 6,692,485 | B1 | 2/2004 | Brock et al. |
| 6,889,116 | B2 | 5/2005 | Jinno |
| 6,936,042 | B2 | 8/2005 | Wallace et al. |
| 6,969,385 | B2 | 11/2005 | Moreyra |
| 6,994,716 | B2 | 2/2006 | Jinno et al. |
| 7,101,363 | B2 | 9/2006 | Nishizawa et al. |
| 7,338,513 | B2 | 3/2008 | Lee et al. |
| 7,364,582 | B2 | 4/2008 | Lee |
| 7,540,867 | B2 | 6/2009 | Jinno et al. |
| 7,648,519 | B2 | 1/2010 | Lee et al. |
| 7,686,826 | B2 | 3/2010 | Lee et al. |
| 7,914,522 | B2 | 3/2011 | Morley et al. |
| 7,942,895 | B2 | 5/2011 | Jinno et al. |
| 8,100,824 | B2 | 1/2012 | Hegeman et al. |
| 8,465,475 | B2 | 6/2013 | Isbell, Jr. |
| 8,801,731 | B2 | 8/2014 | Jeong |
| 8,821,480 | B2 | 9/2014 | Burbank |
| 9,033,998 | B1 | 5/2015 | Schaible et al. |
| 9,179,927 | B2 | 11/2015 | Stefanchik et al. |
| 9,695,916 | B2 | 7/2017 | Lee |
| 9,737,302 | B2 | 8/2017 | Shelton, IV et al. |
| 10,105,128 | B2 | 10/2018 | Cooper et al. |
| 10,166,082 | B1 | 1/2019 | Hariri et al. |
| 10,405,936 | B2 | 9/2019 | Awtar et al. |
| 2003/0036748 | A1 | 2/2003 | Cooper et al. |
| 2004/0199147 | A1 | 10/2004 | Nishizawa et al. |
| 2005/0096694 | A1 | 5/2005 | Lee |
| 2006/0020287 | A1 | 1/2006 | Lee |
| 2006/0190034 | A1 | 8/2006 | Nishizawa |
| 2006/0219065 | A1 | 10/2006 | Jinno et al. |
| 2007/0208375 | A1 | 9/2007 | Nishizawa et al. |
| 2007/0265502 | A1 | 11/2007 | Minosawa et al. |
| 2008/0000317 | A1 | 1/2008 | Patton |
| 2008/0039255 | A1 | 2/2008 | Jinno |
| 2008/0065116 | A1 | 3/2008 | Lee et al. |
| 2008/0245175 | A1 | 10/2008 | Jinno et al. |
| 2009/0112230 | A1 | 4/2009 | Jinno |
| 2010/0198253 | A1 | 8/2010 | Jinno |
| 2010/0249818 | A1 | 9/2010 | Jinno |
| 2010/0286480 | A1 | 11/2010 | Peine et al. |
| 2011/0106145 | A1 | 5/2011 | Jeong |
| 2011/0112517 | A1 | 5/2011 | Peine |
| 2012/0004648 | A1 | 1/2012 | Choi et al. |
| 2012/0330287 | A1 | 12/2012 | Yim |
| 2013/0012958 | A1 | 1/2013 | Marczyk et al. |
| 2013/0012959 | A1 | 1/2013 | Jinno |
| 2013/0144274 | A1 | 6/2013 | Stefanchik et al. |
| 2014/0114293 | A1 | 4/2014 | Jeong et al. |
| 2014/0194893 | A1 | 7/2014 | Jeong et al. |
| 2014/0318288 | A1 | 10/2014 | Lee |
| 2014/0350570 | A1 | 11/2014 | Lee |
| 2015/0032125 | A1 | 1/2015 | Jeong et al. |
| 2015/0150635 | A1 | 6/2015 | Kilroy et al. |
| 2016/0008068 | A1 | 1/2016 | Hyodo et al. |
| 2016/0256232 | A1 | 9/2016 | Awtar et al. |
| 2017/0042560 | A1 | 2/2017 | Lee et al. |
| 2018/0110577 | A1 | 4/2018 | Lee et al. |
| 2018/0228506 | A1 | 8/2018 | Lee et al. |
| 2019/0336230 | A1 | 11/2019 | Awtar et al. |

FOREIGN PATENT DOCUMENTS

| | | | | |
|---|---|---|---|---|
| JP | 64-49739 | A | 2/1989 | |
| JP | H06-311984 | A | 11/1994 | |
| JP | H08173442 | A | 7/1996 | |
| JP | 2004-122286 | A | 4/2004 | |
| JP | 200634978 | A | 2/2006 | |
| JP | 2006-061364 | A | 3/2006 | |
| JP | 2006-062019 | A | 3/2006 | |
| JP | 2006-116194 | A | 5/2006 | |
| JP | 2008-521485 | A | 6/2008 | |
| JP | 2010-220786 | A | 10/2010 | |
| JP | 4701433 | B2 | 3/2011 | |
| JP | 2011/521703 | A | 7/2011 | |
| JP | 2011-200666 | A | 10/2011 | |
| KR | 10-2006-0093060 | A | 8/2006 | |
| KR | 10-0695471 | B1 | 3/2007 | |
| KR | 10-2009-0119366 | A | 11/2009 | |
| KR | 10-2009-0124828 | A | 12/2009 | |
| KR | 10-0956760 | B1 | 5/2010 | |
| KR | 10-2010-0099818 | A | 9/2010 | |
| KR | 10-2010-0118573 | A | 11/2010 | |
| KR | 10-2011-0005671 | A | 1/2011 | |
| KR | 10-2011-0014534 | A | 2/2011 | |
| KR | 10-2011-0028613 | A | 3/2011 | |
| KR | 101064825 | B1 | 9/2011 | |
| KR | 10-1075294 | B1 | 10/2011 | |
| KR | 10-2012-0003091 | A | 1/2012 | |
| KR | 10-2013-0023311 | A | 3/2013 | |
| KR | 10-2013-0023755 | A | 3/2013 | |
| KR | 10-2013-0057250 | A | 5/2013 | |
| KR | 10-1301783 | B1 | 8/2013 | |
| KR | 10-1364970 | B1 | 2/2014 | |
| KR | 10-2014-0113893 | A | 9/2014 | |
| WO | 2009/100366 | A2 | 8/2009 | |
| WO | 2009158115 | A1 | 12/2009 | |
| WO | 2010/030114 | A2 | 3/2010 | |
| WO | 2011/115311 | A1 | 9/2011 | |
| WO | 2012074564 | A1 | 6/2012 | |
| WO | 2013/077571 | A1 | 5/2013 | |
| WO | WO-2013077571 | A * | 5/2013 | ............ A61B 17/29 |
| WO | 2013082220 | A2 | 6/2013 | |
| WO | 2014/123390 | A1 | 8/2014 | |
| WO | 2014/156219 | A1 | 10/2014 | |

\* cited by examiner

[Fig. 1a]
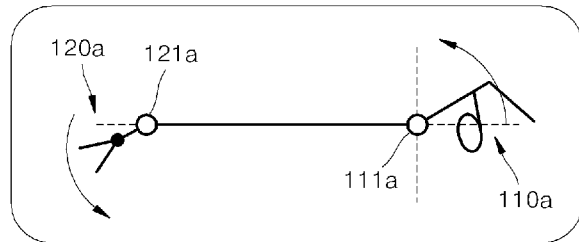
[Fig. 1b]
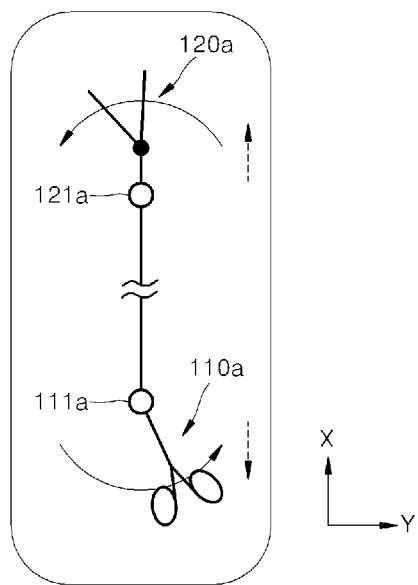
[Fig. 1c]
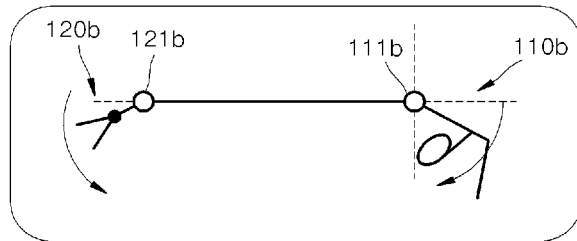

[Fig. 1d]
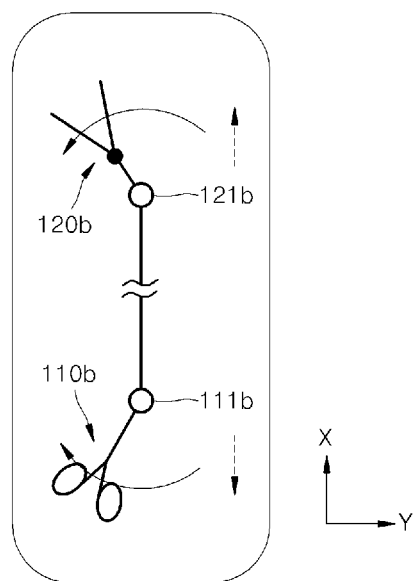
[Fig. 1e]
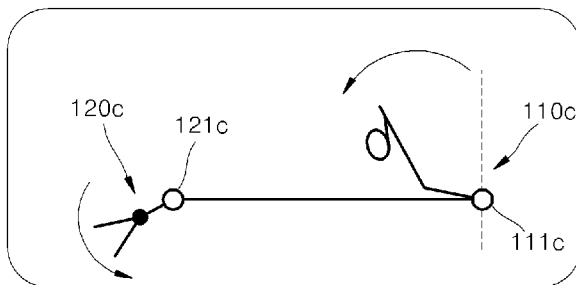
[Fig. 1f]
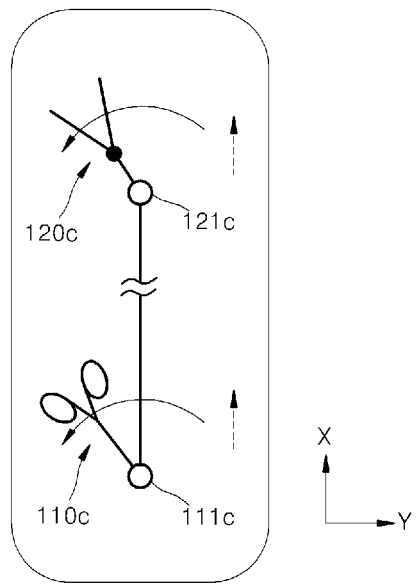

[Fig. 2]
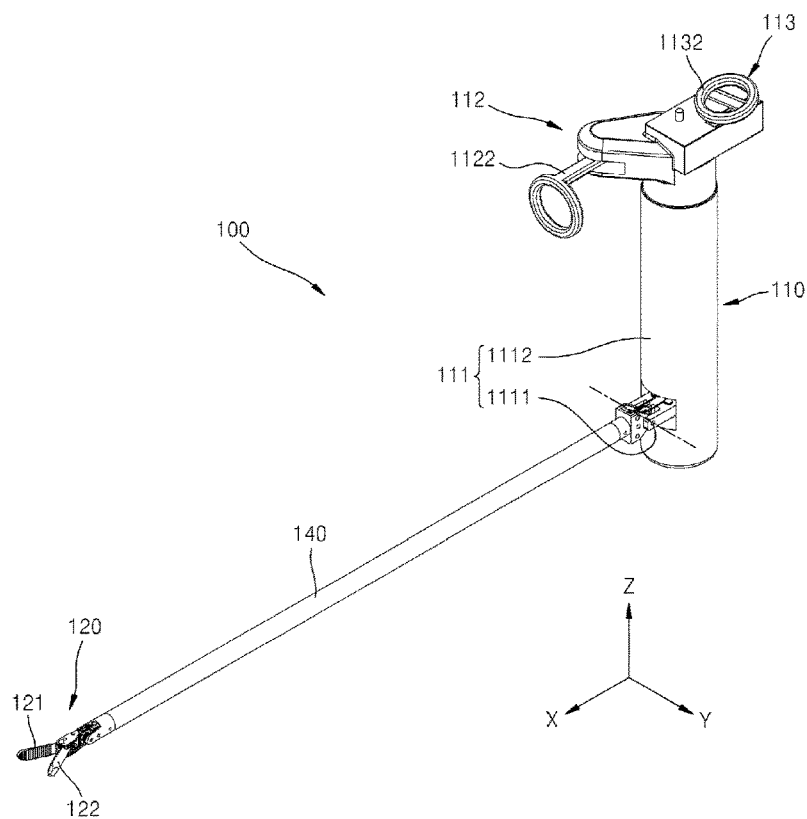
[Fig. 3]
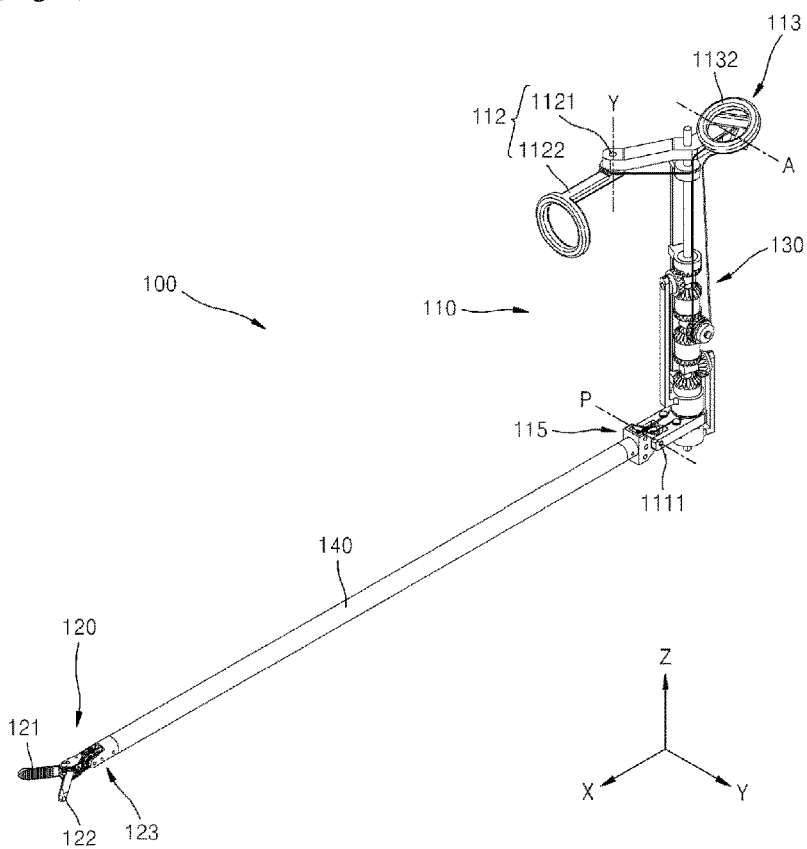

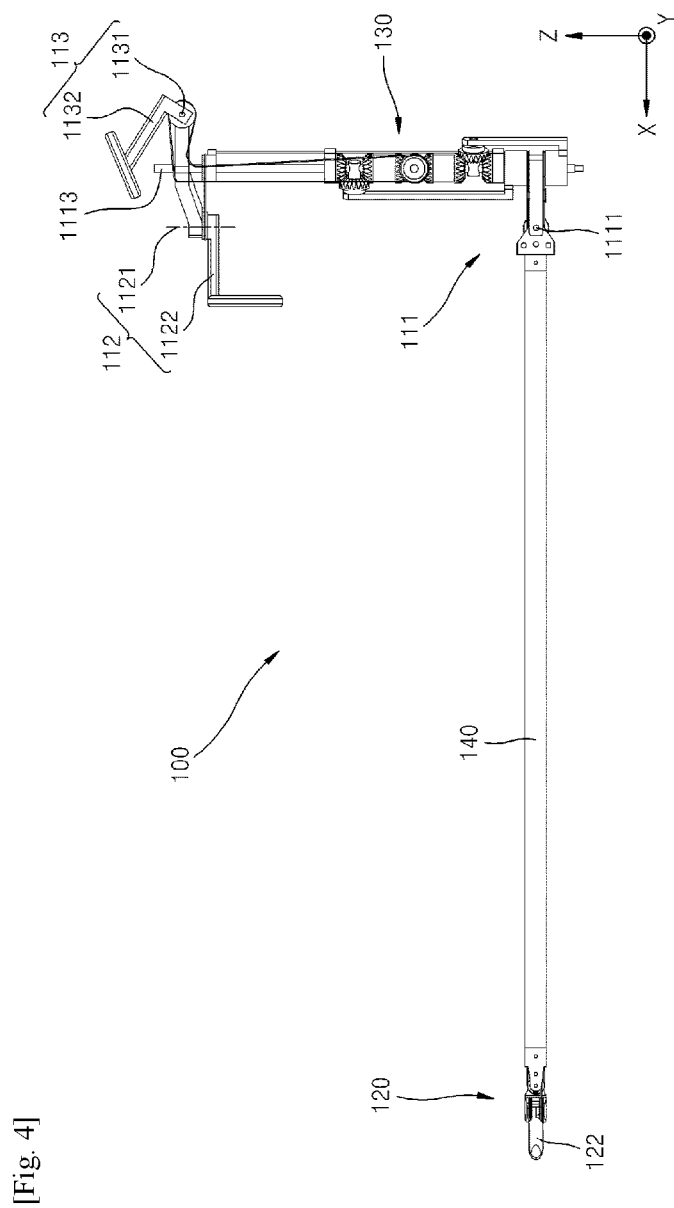
[Fig. 4]

[Fig. 5]
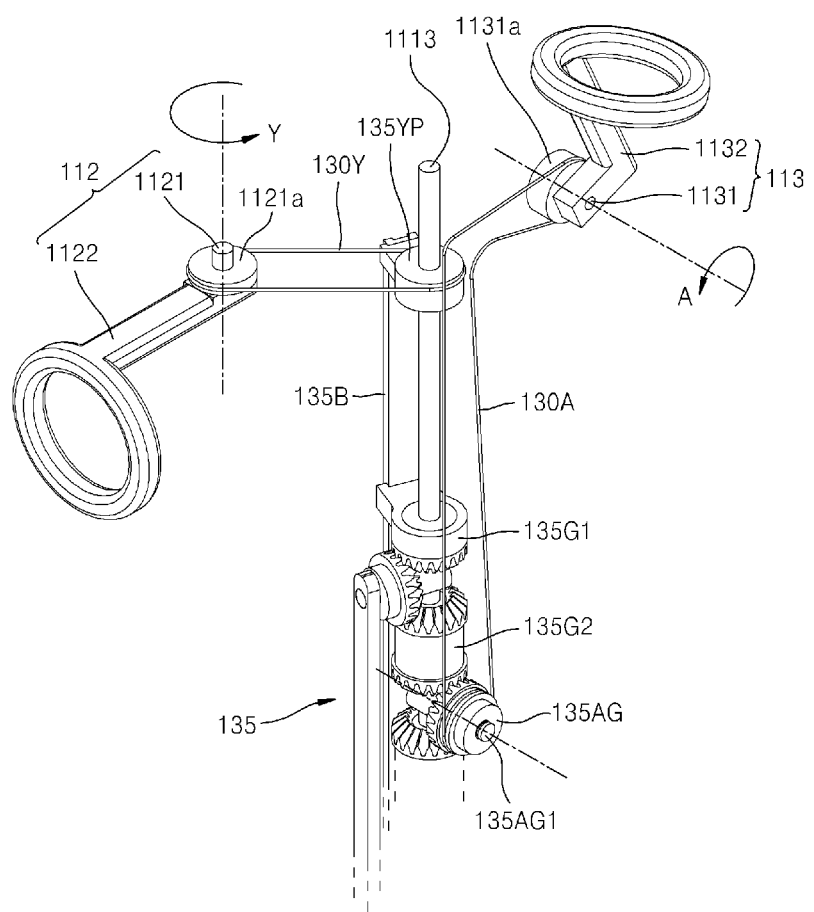

[Fig. 6]
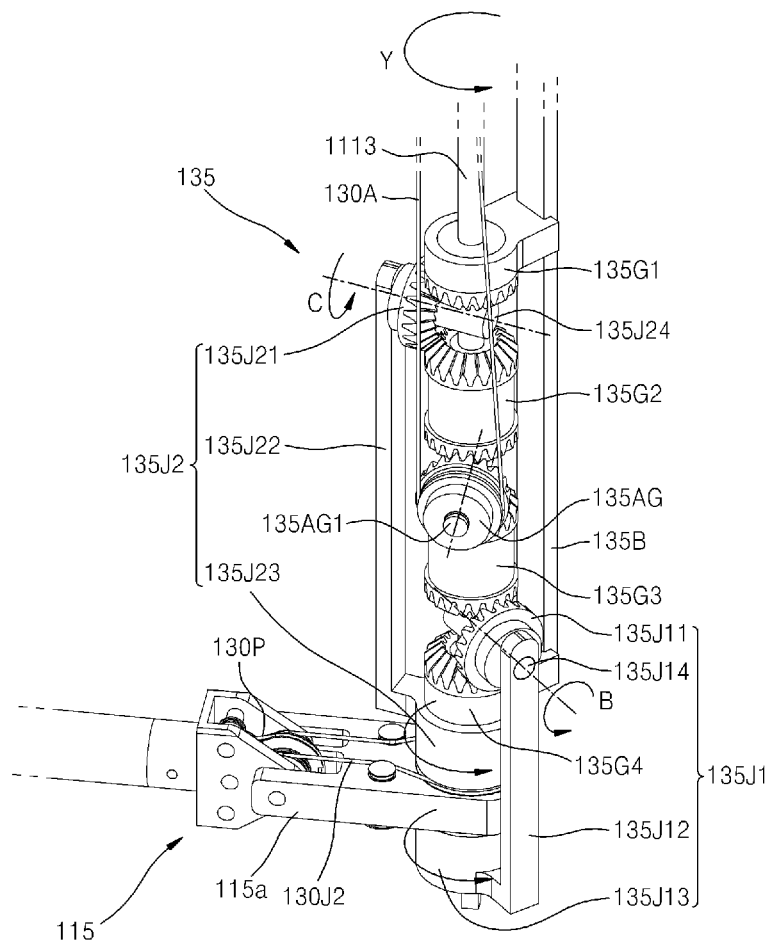
[Fig. 7]
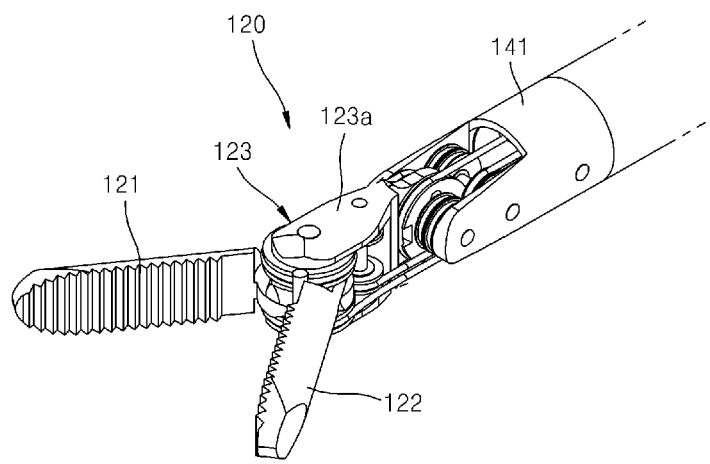

[Fig. 8]
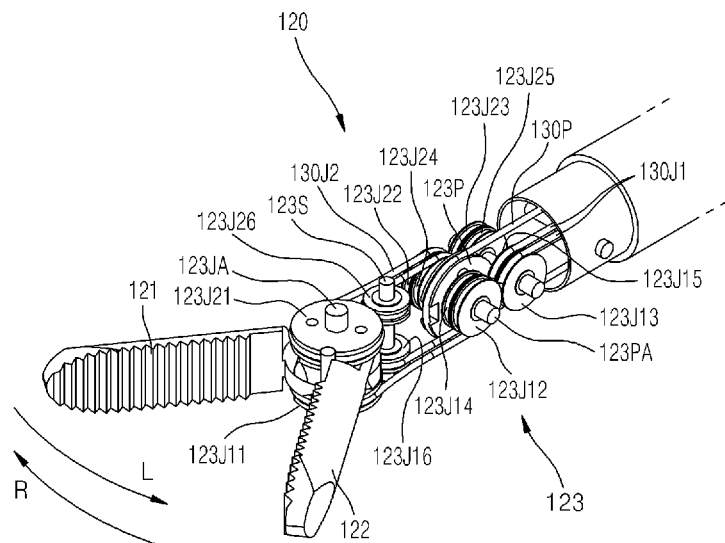
[Fig. 9a]
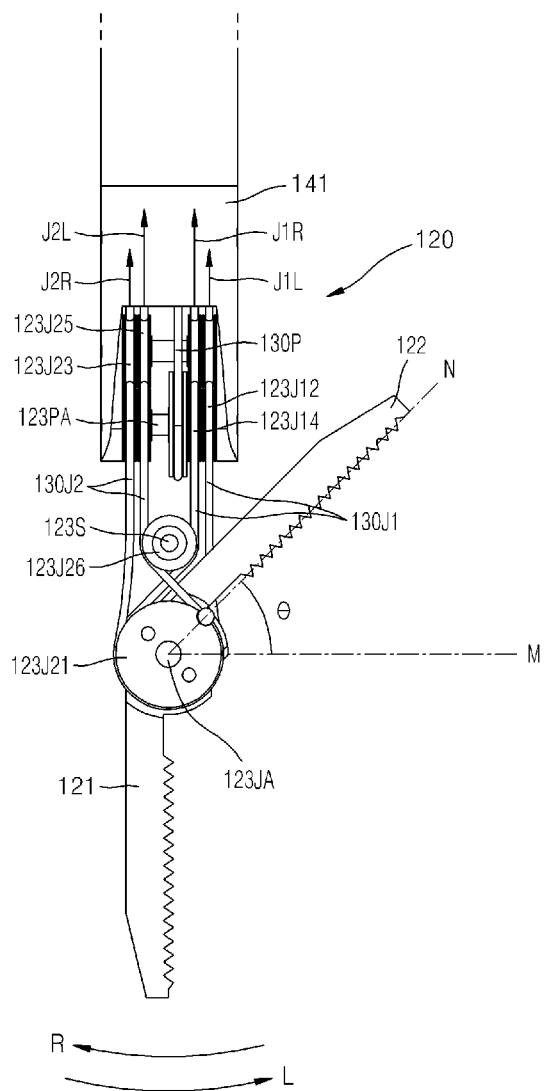

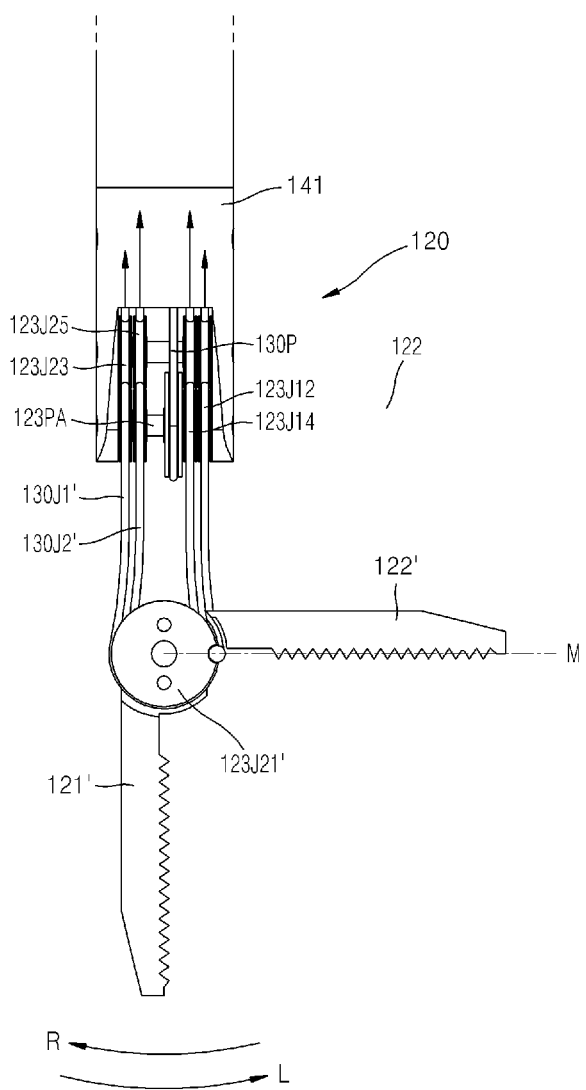
[Fig. 9b]

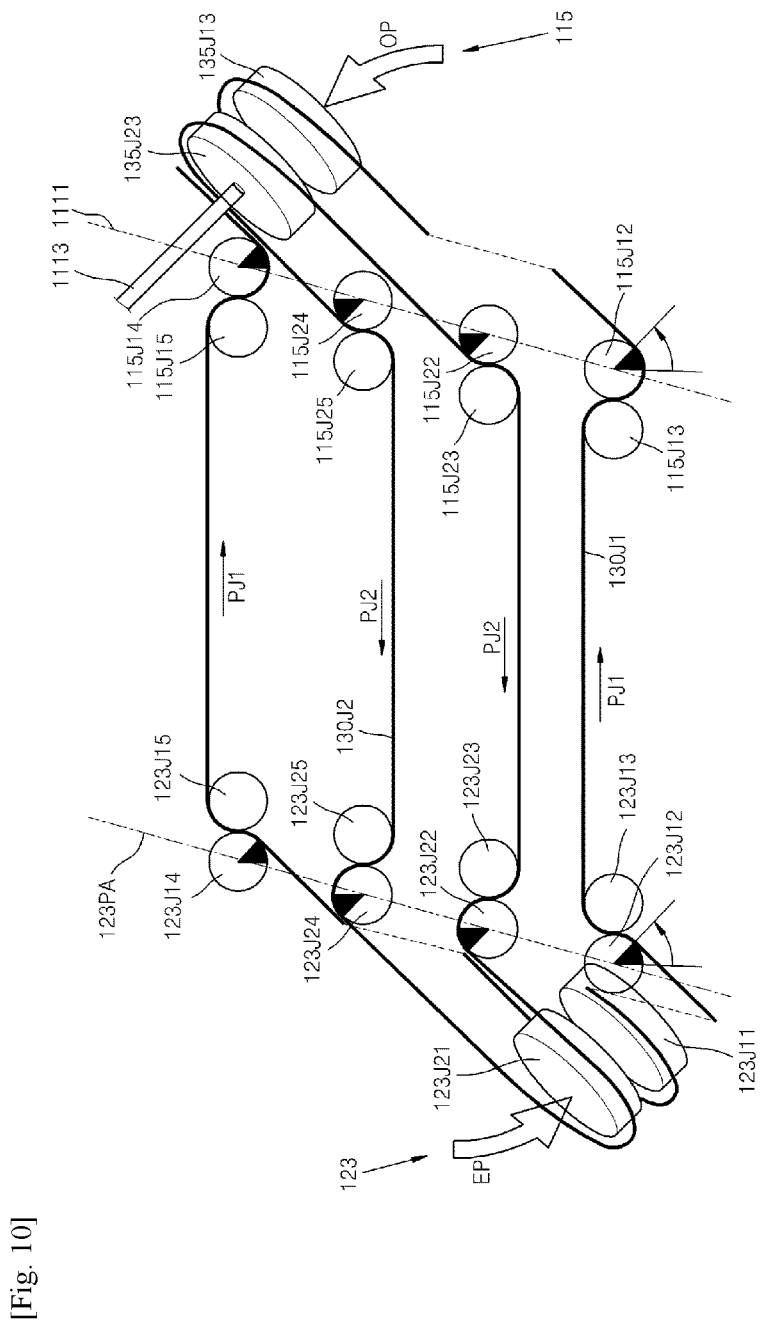
[Fig. 10]

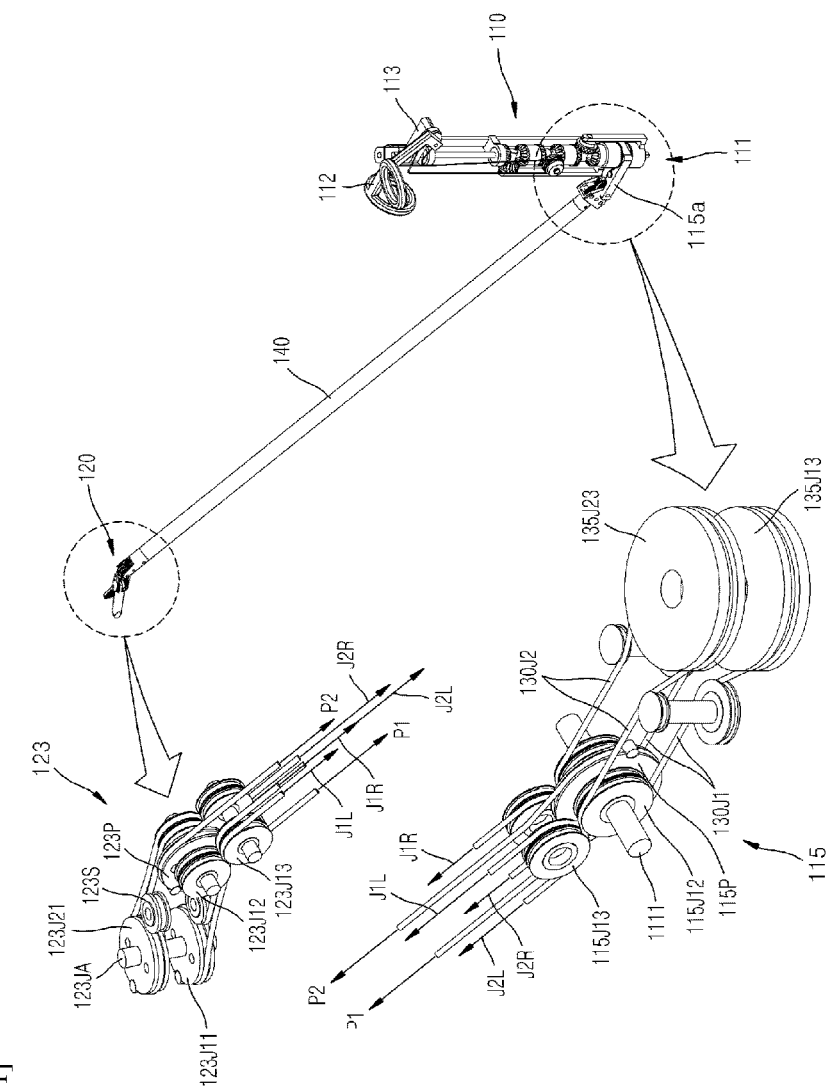
[Fig. 11]

[Fig. 12]
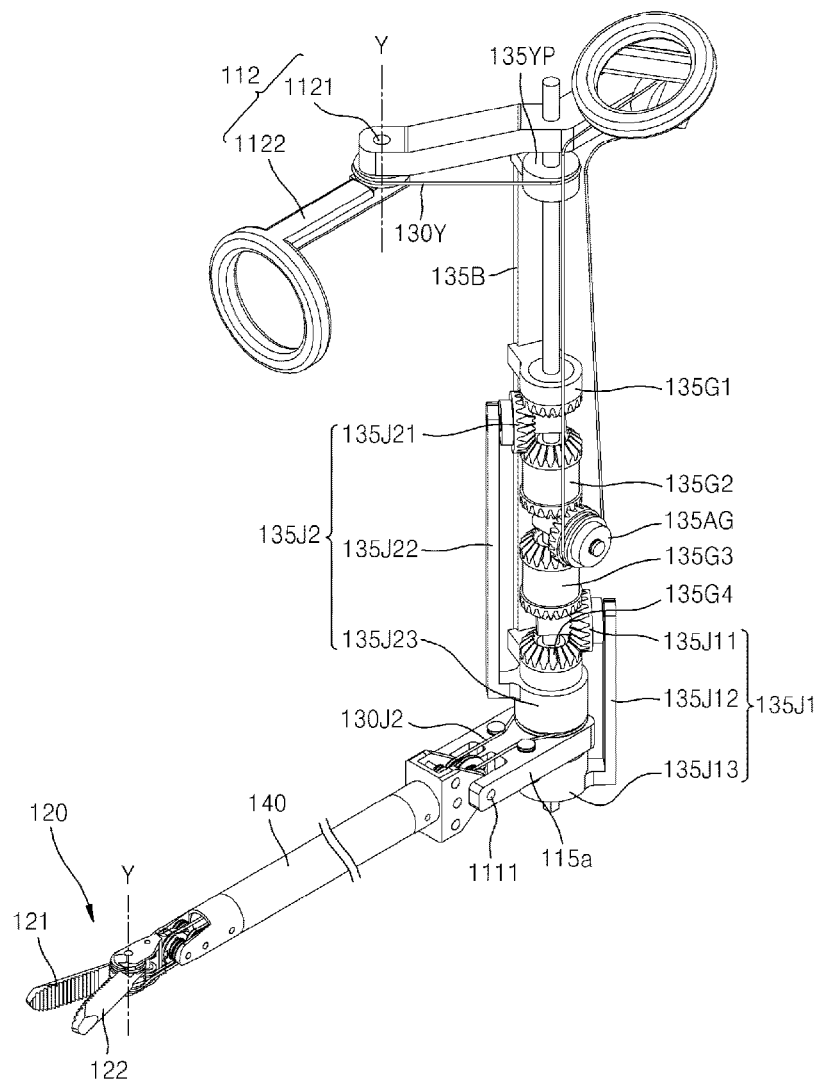

[Fig. 13]
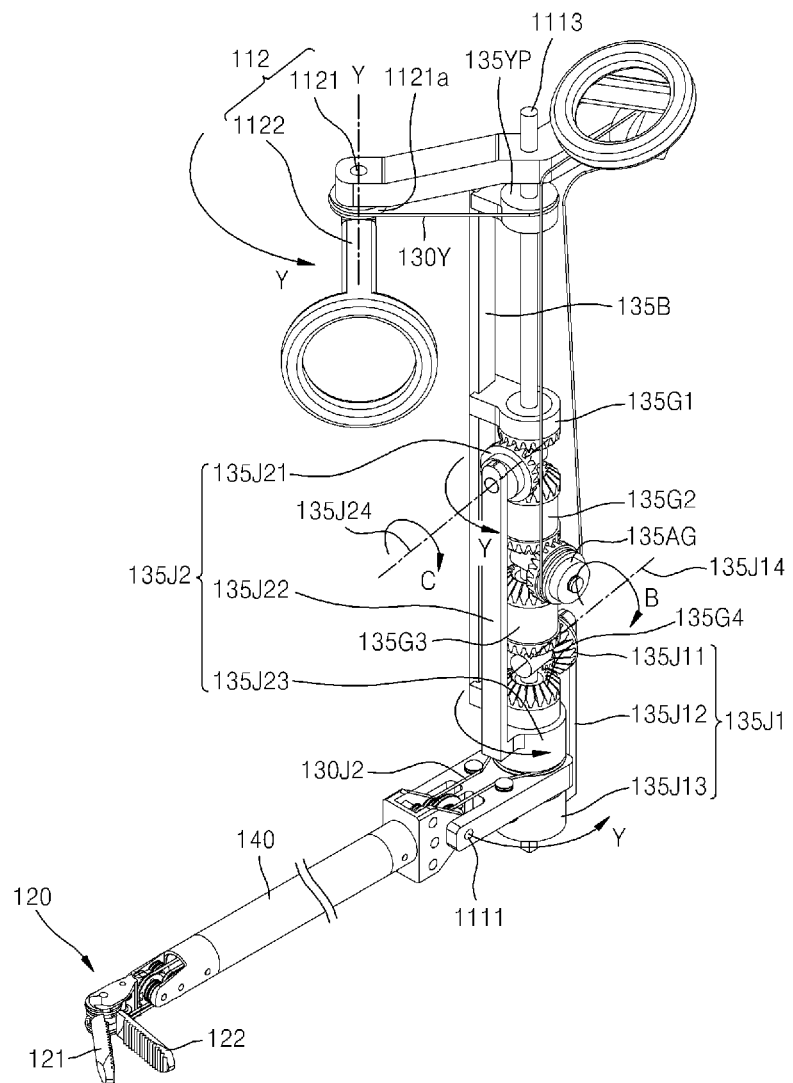

[Fig. 14]
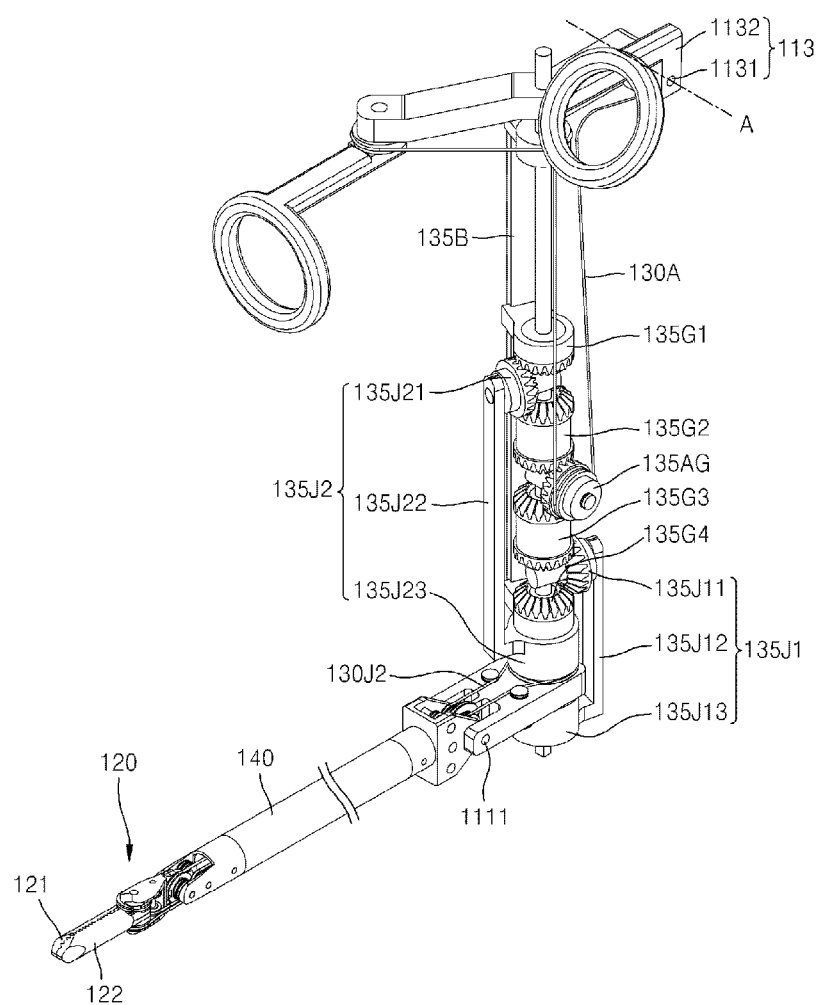

[Fig. 15]
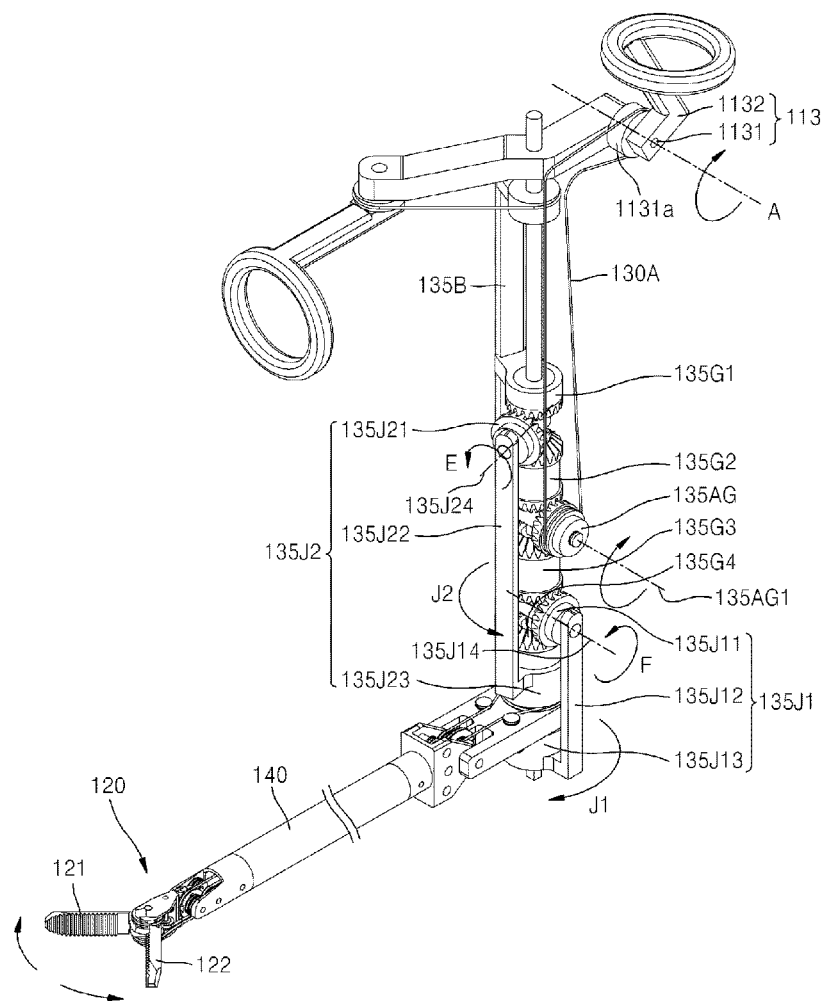

[Fig. 16]
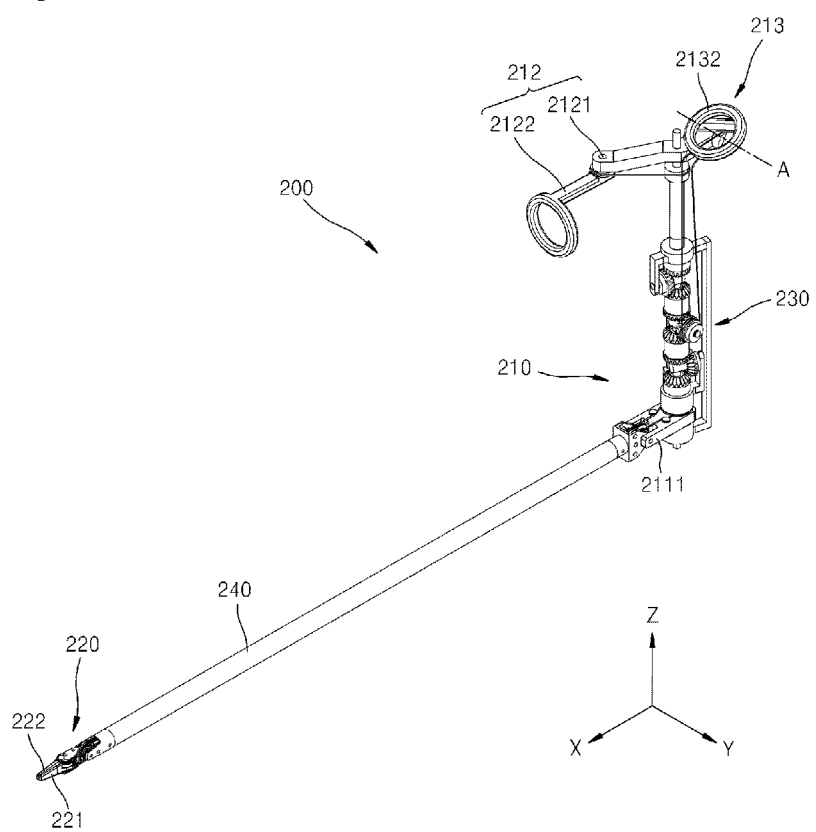

[Fig. 17]
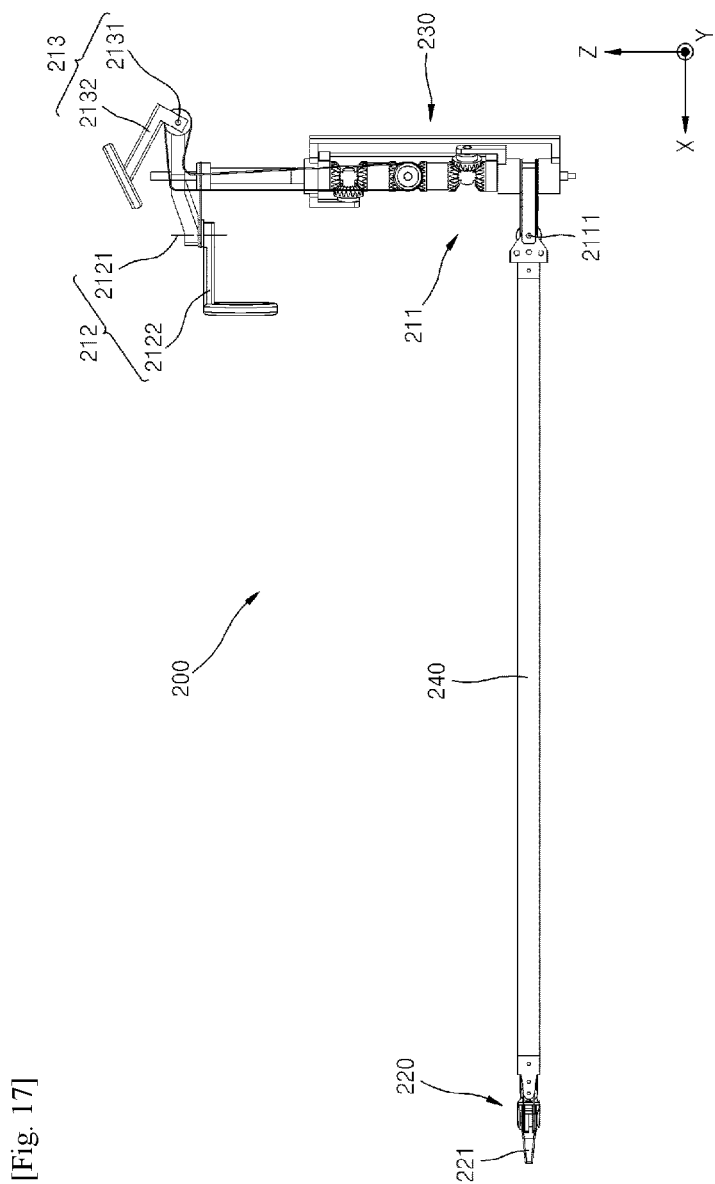

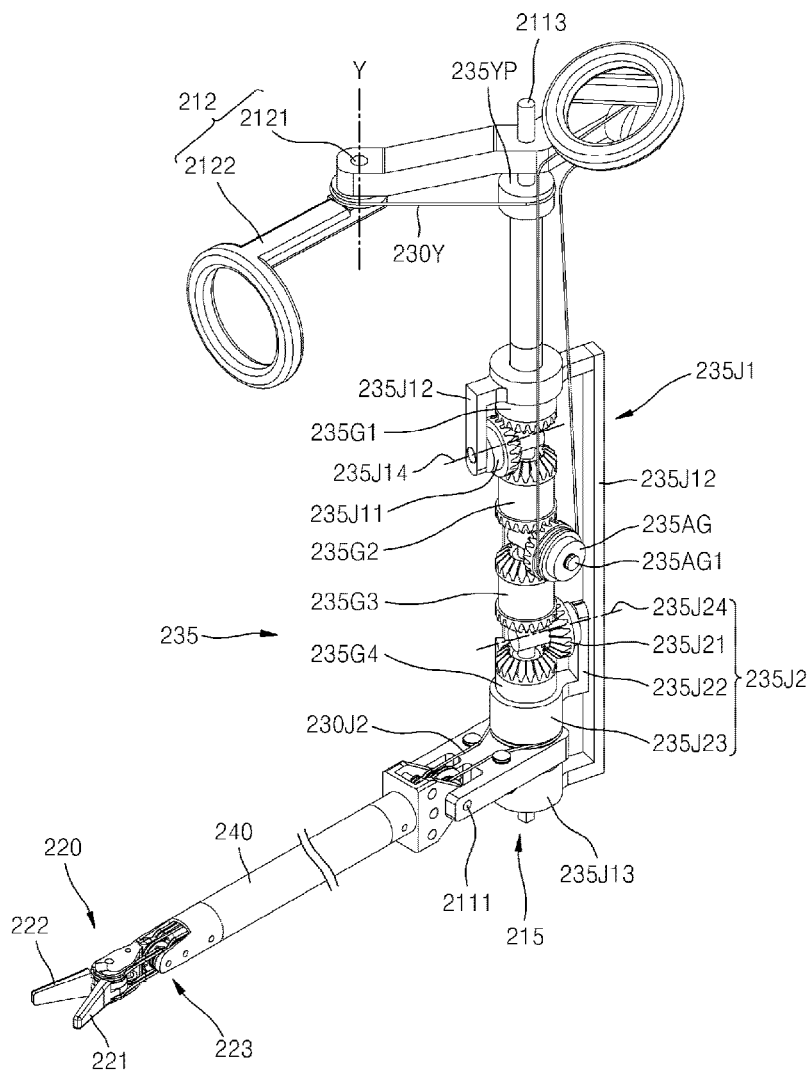
[Fig. 18]

[Fig. 19]
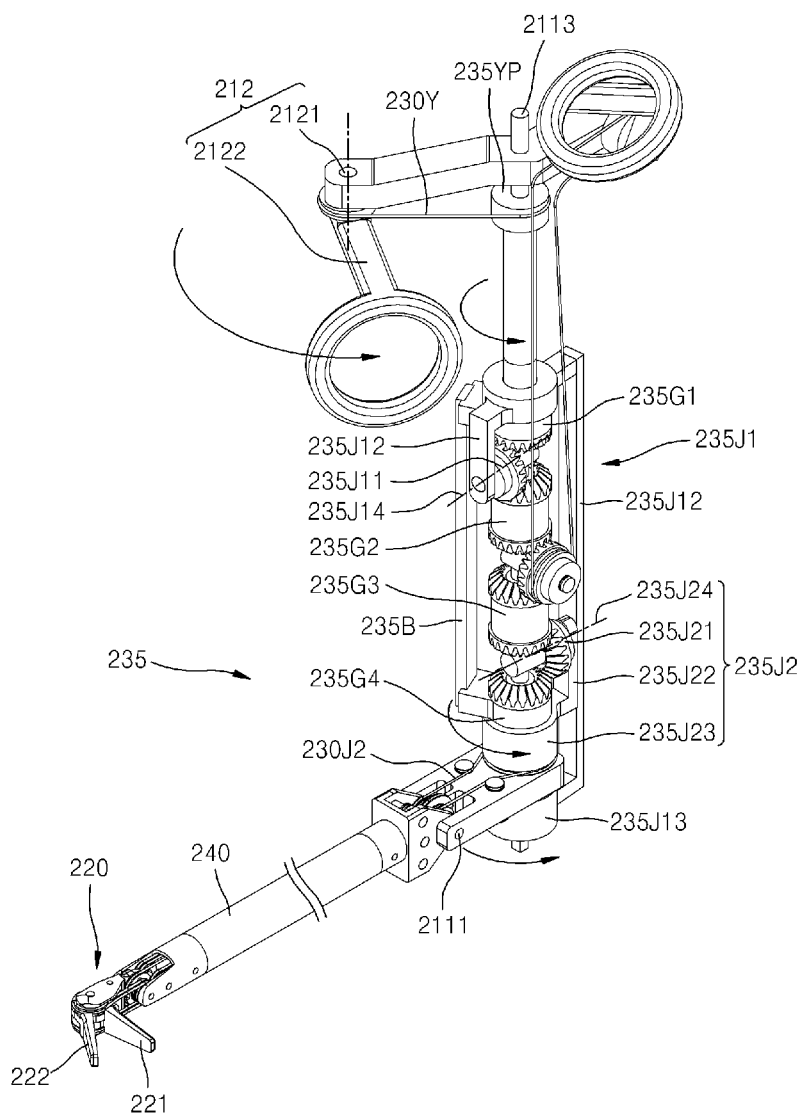

[Fig. 20]
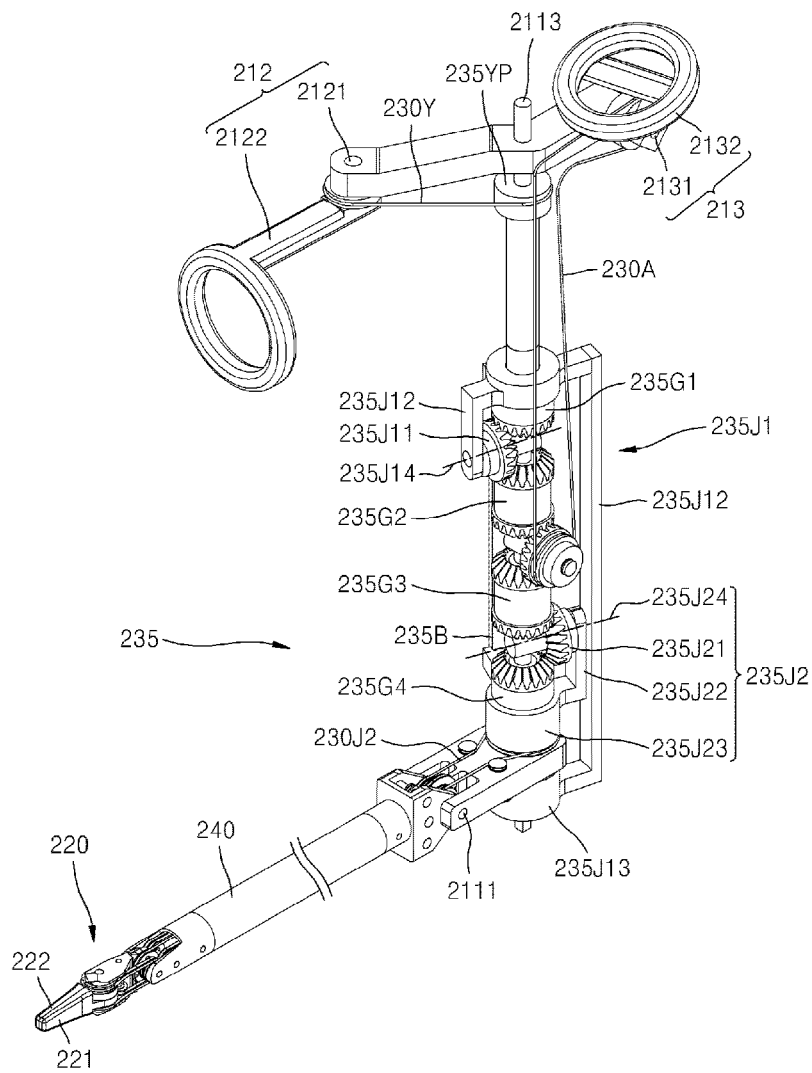

[Fig. 21]
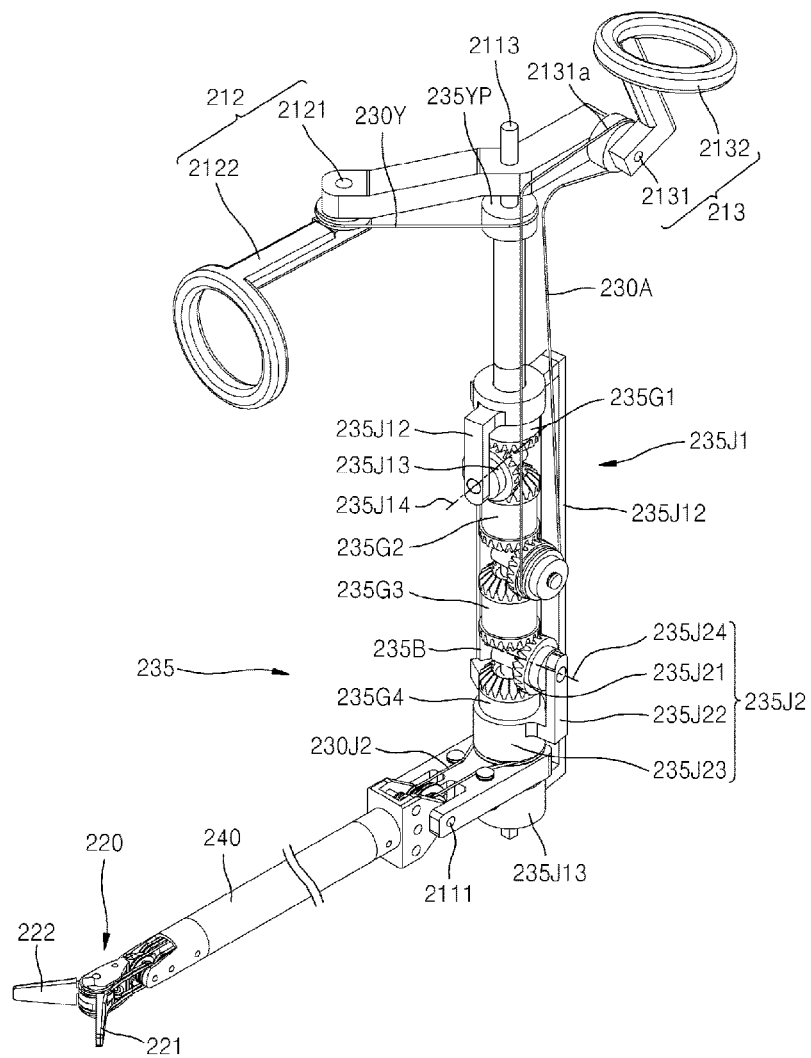

SURGICAL INSTRUMENT

CROSS-REFERENCE TO RELATED APPLICATIONS

This application is a divisional application of U.S. application Ser. No. 15/306,371 filed on Oct. 24, 2016, which is a national stage application under 35 USC § 371 of PCT/KR2014/009599 filed on Oct. 14, 2014, and claims priority to Korean patent application No. 10-2014-0049460 filed on Apr. 24, 2014, the disclosures of which are incorporated herein by reference in their entirety.

TECHNICAL FIELD

The present invention relates to surgical instruments, and more particularly, to surgical instruments that may be manually operated to perform laparoscopic operations or various surgical operations.

BACKGROUND ART

A surgical operation is an operation for curing a disease by cutting, incising, and processing skin, membranes, or other tissues by using medical instruments. However, open surgery, which cuts and opens the skin of a surgical region and cures, shapes, or removes an organ therein, may cause bleeding, side effects, pain, scars, or the like. Therefore, a surgical operation, which is performed by forming a hole through the skin and inserting a medical instrument, for example, a laparoscope, a surgical instrument, or a surgical microscope thereinto, or a robotic surgical operation have recently become popular alternatives.

The surgical instrument is an instrument for performing, by a surgeon, an operation on a surgical region by operating an end tool, which is installed at one end of a shaft inserted into a hole formed through the skin, by using an operator or by using a robotic arm. The end tool provided in the surgical instrument performs a rotating operation, a gripping operation, a cutting operation, or the like through a predetermined structure.

However, since a conventional surgical instrument uses an unbendable end tool, it is not suitable for accessing a surgical region and performing various surgical operations. In order to solve this problem, a surgical instrument having a bendable end tool has been developed. However, an operation of an operator for bending the end tool to perform a surgical operation is not intuitively identical to an actual bending operation of the end tool for performing the surgical operation. Therefore, for surgical operators, it is difficult to perform an intuitive operation, and it takes a long time to learn how to use the surgical instrument.

Information disclosed in this Background section was already known to the inventors before achieving the present invention or is technical information acquired in the process of achieving the present invention. Therefore, it may contain information that does not form the prior art that is already known to the public in this country.

DETAILED DESCRIPTION OF THE INVENTION

Technical Problem

The present invention provides a surgical instrument that is configured to intuitively match an actual operation of bending an end tool or performing a surgical operation with a corresponding operation of an operator. More particularly, to this end, the present invention provides an end tool having various degrees of freedom, an operator configured to intuitively control an operation of the end tool, and an operating force transmitter configured to transmit an operating force of the operator so that the end tool may operate in accordance with an operation of the operator.

Technical Solution

According to an embodiment of the present invention, a surgical instrument includes: an end tool including a first jaw and a second jaw configured to rotate independently; an operator including a pitch operator controlling a pitch motion of the end tool, a yaw operator controlling a yaw motion of the end tool, and an actuation operator controlling an actuation motion of the end tool; an operating force transmitter including a first jaw wire connected with the first jaw to transmit an operation of the operator to the first jaw, a second jaw wire connected with the second jaw to transmit an operation of the operator to the second jaw, and one or more differential members transmitting a rotation of the yaw operator or the actuation operator to the first jaw or the second jaw via the first jaw wire or the second jaw wire; and a connector configured to extend in a first direction (X axis) and having one end portion coupled to the end tool and the other end portion coupled to the operator to connect the operator and the end tool, wherein the pitch operator is configured to rotate around a second direction (Y axis) perpendicular to the first direction; and at least a portion of the operator is configured to be more adjacent to the end tool than a rotating axis of the operator in at least any one operation state of the operator.

According to another embodiment of the present invention, an end tool includes: a first jaw and a second jaw configured to rotate independently of each other; a J11 pulley coupled with the first jaw and configured to rotate around a first axis formed at an end tool hub; a J16 pulley formed at one side of the J11 pulley and configured to rotate around a second axis formed at one side of the first axis; a J12 pulley and a J14 pulley formed at one side of the J16 pulley, and configured to rotate around a third axis formed at a predetermined angle with the first axis, and formed at one side of the end tool hub; a J21 pulley coupled with the second jaw and configured to rotate around an axis that is substantially identical to or parallel to the first axis; a J26 pulley formed at one side of the J21 pulley and configured to rotate around an axis that is substantially identical to or parallel to the second axis; and a J22 pulley and a J24 pulley formed at one side of the J26 pulley and configured to rotate around an axis that is substantially identical to or parallel to the third axis, wherein a first jaw wire is configured to at least partially contact the J12 pulley, the J11 pulley, the J16 pulley, and the J14 pulley; and a second jaw wire is configured to at least partially contact the J22 pulley, the J21 pulley, the J26 pulley, and the J24 pulley.

These and/or other aspects will become apparent and more readily appreciated from the following description of the invention, taken in conjunction with the accompanying drawings.

Advantageous Effects of the Invention

According to the present invention, since an operation direction of the operator by a surgical operator and an operation direction of the end tool are intuitively identical to each other, the convenience of the surgical operator may be improved, and the accuracy, reliability, and the quickness of a surgical operation may be improved.

DESCRIPTION OF THE DRAWINGS

FIG. 1A is a schematic diagram illustrating a pitch operation of a conventional surgical instrument, and FIG. 1B is a schematic diagram illustrating a yaw operation thereof.

FIG. 1C is a schematic diagram illustrating a pitch operation of another conventional surgical instrument, and FIG. 1D is a schematic diagram illustrating a yaw operation thereof.

FIG. 1E is a schematic diagram illustrating a pitch operation of a surgical instrument according to the present invention, and FIG. 1F is a schematic diagram illustrating a yaw operation thereof.

FIG. 2 is a perspective view of a surgical instrument according to a first embodiment of the present invention.

FIG. 3 is an internal perspective view of the surgical instrument of FIG. 2.

FIG. 4 is a side view of the surgical instrument of FIG. 3.

FIG. 5 is a perspective view illustrating an upper portion of an operator of the surgical instrument of FIG. 3.

FIG. 6 is a perspective view illustrating a lower portion of the operator of the surgical instrument of FIG. 3.

FIGS. 7 and 8 are perspective views illustrating an end tool of the surgical instrument of FIG. 3.

FIG. 9A is a plan view illustrating an end tool of the surgical instrument of FIG. 3.

FIG. 9B is a plan view illustrating an end tool of a conventional surgical instrument.

FIG. 10 is a schematic view illustrating a pitch operation of the surgical instrument of FIG. 3.

FIG. 11 is a perspective view illustrating a pitch operation of the surgical instrument of FIG. 3.

FIGS. 12 and 13 are views illustrating a yaw operation of the surgical instrument of FIG. 3.

FIGS. 14 and 15 are views illustrating an actuation operation of the surgical instrument of FIG. 3.

FIG. 16 is a perspective view of a surgical instrument according to a second embodiment of the present invention.

FIG. 17 is a plan view of the surgical instrument of FIG. 16.

FIG. 18 is a perspective view illustrating an operator of the surgical instrument of FIG. 16.

FIG. 19 is a view illustrating a yaw operation of the surgical instrument of FIG. 16.

FIGS. 20 and 21 are views illustrating an actuation operation of the surgical instrument of FIG. 16.

BEST MODE

The present invention may include various embodiments and modifications, and particular embodiments thereof are illustrated in the drawings and will be described herein in detail. However, it will be understood that the present invention is not limited to the embodiments and includes all modifications, equivalents and substitutions falling within the spirit and scope of the present invention. In the following description, detailed descriptions of well-known functions or configurations will be omitted since they would unnecessarily obscure the subject matters of the present invention.

Although terms such as "first" and "second" may be used herein to describe various elements or components, these elements or components should not be limited by these terms. These terms are only used to distinguish one element or component from another element or component.

The terminology used herein is for the purpose of describing particular embodiments only and is not intended to limit the present invention. As used herein, the singular forms "a", "an", and "the" are intended to include the plural forms as well, unless the context clearly indicates otherwise. It will be understood that terms such as "comprise", "include", and "have", when used herein, specify the presence of stated features, integers, steps, operations, elements, components, or combinations thereof, but do not preclude the presence or addition of one or more other features, integers, steps, operations, elements, components, or combinations thereof.

Hereinafter, embodiments of the present invention will be described in detail with reference to the accompanying drawings. In the following description, like reference numerals denote like elements, and redundant descriptions thereof will be omitted.

Also, it will be understood that various embodiments of the present invention may be interpreted or implemented in combination, and technical features of each embodiment may be interpreted or implemented in combination with technical features of other embodiments.

First Embodiment of Surgical Instrument

A surgical instrument according to the present invention is characterized in that, for at least any one of the pitch, yaw, and actuation operations, when an operator is rotated in any one direction, an end tool rotates in a direction that is intuitively identical to an operation direction of the operator.

FIG. 1A is a schematic diagram illustrating a pitch operation of a conventional surgical instrument, and FIG. 1B is a schematic diagram illustrating a yaw operation thereof.

Referring to FIG. 1A, in order to perform a pitch operation of a conventional surgical instrument, in a state where an end tool 120a is formed in front of an end tool rotation center 121a and an operator 110a is formed in back of an operator rotation center 111a, when the operator 110a is rotated in a clockwise direction, the end tool 120a also rotates in the clockwise direction, and when the operator 110a is rotated in a counterclockwise direction, the end tool 120a also rotates in the counterclockwise direction. Referring to FIG. 1B, in order to perform a yaw operation of a conventional surgical instrument, in a state where an end tool 120a is formed in front of an end tool rotation center 121a and an operator 110a is formed in back of an operator rotation center 111a, when the operator 110a is rotated in a clockwise direction, the end tool 120a also rotates in the clockwise direction, and when the operator 110a is rotated in a counterclockwise direction, the end tool 120a also rotates in the counterclockwise direction. In this case, from the viewpoint of a horizontal direction of a user, when the user moves the operator 110a to the left, the end tool 120a moves to the right, and when the user moves the operator 110a to the right, the end tool 120a moves to the left. Consequently, since the operation direction of the user and the operation direction of the end tool are opposite to each other, the user may make an error and the operation of the user may not be easy.

FIG. 1C is a schematic diagram illustrating a pitch operation of another conventional surgical instrument, and FIG. 1D is a schematic diagram illustrating a yaw operation thereof.

Referring to FIG. 1C, in order for another conventional surgical instrument to be mirror-symmetrically formed to perform a pitch operation, in a state where an end tool 120b is formed in front of an end tool rotation center 121b and an operator 110b is formed in back of an operator rotation center 111b, when the operator 110b is rotated in the clockwise direction, the end tool 120b rotates in the counterclockwise direction, and when the operator 110b is rotated in the counterclockwise direction, the end tool 120b rotates in the clockwise direction. In this case, from the viewpoint of the rotation direction of the operator and the end tool, the rotation direction of the operator 110b by the user and the corresponding rotation direction of the end tool 120b are opposite to each other. Consequently, the user may confuse the operation direction, the operation of a joint may not be intuitive, and an error may be caused accordingly. Also, referring to FIG. 1D, in order to perform a yaw operation, in a state where an end tool 120b is formed in front of an end tool rotation center 121b and an operator 110b is formed in back of an operator rotation center 111b, when the operator 110b is rotated in the clockwise direction, the end tool 120b rotates in the counterclockwise direction, and when the operator 110b is rotated in the counterclockwise direction, the end tool 120b rotates in the clockwise direction. In this case, from the viewpoint of the rotation direction of the operator and the end tool, the rotation direction of the operator 110b by the user and the corresponding rotation direction of the end tool 120b are opposite to each other. Consequently, the user may confuse the operation direction, the operation of a joint may not be intuitive, and an error may be caused accordingly.

In order to solve this problem, a surgical instrument according to an embodiment of the present invention illustrated in FIGS. 1E and 1F is characterized in that an end tool 120c is formed in front of an end tool rotation center 121c and an operator 110c is also formed in front of an operator rotation center 111c, so that the operations of the operator 110c and the end tool 120c are intuitively identical to each other.

In other words, unlike a conventional example of the configuration in which the operator becomes adjacent to the user (i.e., becomes distant from the end tool) with respect to its own joint as illustrated in FIGS. 1A, 1B, 1C, and 1D, the surgical instrument according to an embodiment of the present invention illustrated in FIGS. 1E and 1F is formed such that at least a portion of the operator may become more adjacent to the end tool with respect to its own joint (i.e., than its own joint).

In other words, in the case of the conventional surgical instrument illustrated in FIGS. 1A, 1B, 1C, and 1D, since the end tool is located in front of its own rotation center but the operator is formed in back of its own rotation center and thus the end tool moving the front with the rear fixed is moved by the operation of the operator moving the rear with the front fixed, they are not structurally intuitively identical to each other. Consequently, in the operation of the operator and the operation of the end tool, from the viewpoint of the horizontal direction or the viewpoint of the rotation direction, a mismatch may occur, the user may be confused, the operation of the operator may be difficult to perform intuitively rapidly, and an error may be caused accordingly. On the other hand, in the case of the surgical instrument according to an embodiment of the present invention, since both the end tool and the operator move with respect to the rotation center formed at the rear, the operations may be structurally intuitively identical to each other. Consequently, the user may intuitively rapidly control the end tool direction, and the possibility of causing an error may be significantly reduced. A specific mechanism enabling this function will be described below.

FIG. 2 is a perspective view of a surgical instrument according to a first embodiment of the present invention, FIG. 3 is an internal perspective view of the surgical instrument of FIG. 2, and FIG. 4 is a side view of the surgical instrument of FIG. 3.

Referring to FIGS. 2, 3, and 4, a surgical instrument 100 according to a first embodiment of the present invention includes an operator 110, an end tool 120, an operating force transmitter 130, and a connector 140. Herein, the connector 140 may be formed to have the shape of a hollow shaft, so that one or more wires (which will be described later) may be accommodated therein. The operator 110 may be coupled to one end portion of the connector 140, and the end tool 120 may be coupled to the other end portion of the connector 140, so that the connector 140 may connect the operator 110 and the end tool 120.

In detail, the operator 110 is formed at one end portion of the connector 140, and is provided as an interface having, for example, a tweezer shape, a stick shape, or a lever shape, which may be directly operated by a surgical operator. When a surgical operator operates the operator 110, the end tool 120, which is connected to the interface and is inserted into the body of a surgical patient, performs an operation, thereby performing a surgical operation. Although FIG. 2 illustrates that the operator 110 is formed to have the shape of a handle that may be rotated with a finger inserted thereinto, the inventive concept is not limited thereto, and the operator 110 may have various shapes that may be connected with the end tool 120 to operate the end tool 120.

The end tool 120 is formed at the other end portion of the connector 140 and is inserted into a surgical region to perform a necessary surgical operation. As an example of the end tool 120, a pair of jaws, namely, first and second jaws 121 and 122, may be used to perform a grip operation as illustrated in FIG. 2. However, the inventive concept is not limited thereto, and various surgical devices may be used as the end tool 120. For example, a one-armed cautery may be used as the end tool 120. The end tool 120 is connected with the operator 110 by the operating force transmitter 130 to receive an operating force of the operator 110 through the operating force transmitter 130, thereby performing a necessary surgical operation such as a grip, cutting, or suturing.

Herein, the end tool 120 of the surgical instrument 100 according to the first embodiment of the present invention is formed to rotate in two or more directions. For example, the end tool 120 may be formed to perform a pitch motion around a Y axis of FIG. 2 and also perform a yaw motion and an actuation motion around a Z axis of FIG. 2. This will be described later in detail.

The operating force transmitter 130 connects the operator 110 and the end tool 120 to transmit an operating force of the operator 110 to the end tool 120, and may include a plurality of wires, pulleys, links, nodes, and gears.

Hereinafter, the operator 110, the end tool 120, and the operating force transmitter 130 of the surgical instrument 100 of FIG. 2 will be described in more detail.

(Operator) FIG. 5 is a perspective view illustrating an upper portion of the operator of the surgical instrument of FIG. 3, and FIG. 6 is a perspective view illustrating a lower portion of the operator of the surgical instrument of FIG. 3.

Referring to FIGS. 2 to 6, the operator 110 of the surgical instrument 100 according to the first embodiment of the present invention includes a pitch operator 111 controlling a pitch motion of the end tool 120, a yaw operator 112 controlling a yaw motion of the end tool 120, and an actuation operator 113 controlling an actuation motion of the end tool 120.

First, as an example of the use state of the surgical instrument 100 of FIG. 2, the user may grip a pitch operating handle (or bar) 1112 of the pitch operator 111 with the palm and rotate the pitch operating handle 1112 to perform a pitch motion, may insert the index finger into the yaw operator 112 and rotate the yaw operator 112 to perform a yaw motion, and may insert the big finger into the actuation operator 113 and rotate the actuation operator 113 to perform an actuation motion.

A pitch operation, a yaw operation, and an actuation operation used in the present invention are summarized as follows:

First, the pitch operation refers to an operation of rotating the end tool 120 in the vertical direction with respect to the connector 140, that is, an operation of rotating around the Y axis of FIG. 2. In other words, the pitch operation refers to a vertical rotation of the end tool 120, which is formed to extend in the extension direction (the X-axis direction of FIG. 2) of the connector 140, around the Y axis with respect to the connector 140. The yaw operation refers to an operation of rotating the end tool 120 in the horizontal direction with respect to the connector 140, that is, an operation of rotating around the Z axis of FIG. 2. In other words, the yaw operation refers to a horizontal rotation of the end tool 120, which is formed to extend in the extension direction (the X-axis direction of FIG. 2) of the connector 140, around the Z axis with respect to the connector 140. The actuation operation refers a folding or unfolding operation of the jaws 121 and 122 when the jaws 121 and 122 rotate in opposite directions while rotating around the same rotating axis as the yaw operation. That is, the actuation operation refers to rotations of the jaws 121 and 122, which is formed at the end tool 120, in opposite directions around the Z axis.

Herein, when the operator 110 of the surgical instrument 100 is rotated in one direction with respect to the connector 140, the end tool 120 rotates with respect to the connector 140 in a direction that is intuitively identical to an operation direction of the operator 110. In other words, when the pitch operator 111 of the operator 110 rotates in one direction, the end tool 120 rotates in a direction intuitively identical to the one direction to perform a pitch operation, and when the yaw operator 112 of the operator 110 rotates in one direction, the end tool 120 rotates in a direction intuitively identical to the one direction to perform a yaw operation. Herein, it may be said that the intuitively identical direction refers to a case where a movement direction of the index finger of the user gripping the operator 110 is substantially identical to a movement direction of the end portion of the end tool 120. In addition, the identical direction may not be an exactly identical direction on a three-dimensional coordinate system. For example, the identical direction may refer to a case where when the index finger of the user moves to the left, the end portion of the end tool 120 also moves to the left, and when the index finger of the user moves to the right, the end portion of the end tool 120 also moves to the right, in order to maintain intuition.

To this end, in the surgical instrument 100, the operator 110 and the end tool 120 are formed in the same direction with respect to a plane perpendicular to the extension axis (X axis) of the connector 140. That is, in view of a YZ plane of FIG. 2, the operator 110 is formed to extend in a +X-axis direction, and the end tool 120 is also formed to extend in the +X-axis direction. In other words, it may be said that a formation direction of the end tool 120 at one end portion of the connector 140 may be identical to a formation direction of the operator 110 at the other end portion of the connector 140 in view of the YZ plane. In other words, it may be said that the operator 110 is formed to extend away from the body of the user gripping the operator 110, that is, the operator 110 is formed to extend toward the end tool 120.

In detail, in the case of a related art surgical instrument, an operation direction of an operator by a user is different from and is not intuitively identical to an actual operation direction of an end tool. Therefore, a surgical operator has difficulty in performing an intuitive operation, and it takes a long time to skillfully move the end tool in a desired direction. Also, in some cases, a faulty operation may occur, thus damaging a surgical patient.

In order to solve such problems, the surgical instrument 100 according to the first embodiment of the present invention is configured such that an operation direction of the operator 110 is intuitively identical to an operation direction of the end tool 120. To this end, the operator 110 and the end tool 120 are formed on the same side in view of the YZ plane including a pitch operating axis 1111. This will be described below in more detail.

The pitch operator 111 includes a pitch operating axis 1111 and a pitch operating handle 1112. Herein, the pitch operating axis 1111 may be formed in the direction parallel to the Y axis, and the pitch operating handle 1112 may be connected with the pitch operating axis 1111 to rotate along with the pitch operating axis 1111. For example, when the user grips and rotates the pitch operating handle 1112, the pitch operating handle 1112 rotates around the pitch operating axis 1111. Then, the resulting rotating force is transmitted to the end tool 120 through the operating force transmitter 130, an operator control member 115, and an end tool control member 123, so that the end tool 120 rotates in the same direction as the rotation direction of the pitch operator 111. That is, when the pitch operator 111 rotates in the clockwise direction around the pitch operating axis 1111, the end tool 120 also rotates in the clockwise direction around an axis parallel to the pitch operating axis 1111, and when the pitch operator 111 rotates in the counterclockwise direction around the pitch operating axis 1111, the end tool 120 also rotates in the counterclockwise direction around the axis parallel to the pitch operating axis 1111.

The yaw operator 112 and the actuation operator 113 are formed on one end portion of the pitch operating handle 1112 of the pitch operator 111. Thus, when the pitch operator 111 rotates around the pitch operating axis 1111, the yaw operator 112 and the actuation operator 113 also rotate along with the pitch operator 111. FIG. 2 illustrates a state in which the pitch operating handle 1112 of the pitch operator 111 is perpendicular to the connector 140, while FIG. 11 illustrates a state in which the pitch operating handle 1112 of the pitch operator 111 is at an angle to the connector 140 by rotating around the pitch operating axis 1111 by some degree.

Therefore, a coordinate system of the yaw operator 112 and the actuation operator 113 is not fixed, but relatively changes according to the rotation of the pitch operator 111. That is, FIG. 2 illustrates that a yaw operating axis 1121 of the yaw operator 112 is parallel to the Z axis and an actuation operating axis 1131 of the actuation operator 113 is parallel to the Y axis. However, when the pitch operator 111 is rotated, the yaw operating axis 1121 of the yaw operator 112 is not parallel to the Z axis. That is, the coordinate system of the yaw operator 112 and the actuation operator 113 change according to the rotation of the pitch operator 111. However, for convenience of description, the coordinate system of the yaw operator 112 and the actuation operator 113 will be described on the assumption that the pitch operating handle 1112 is perpendicular to the connector 140 as illustrated in FIG. 2.

The yaw operator 112 includes a yaw operating axis 1121 and a yaw operating member 1122. Herein, the yaw operating axis 1121 may be formed to be at a predetermined angle to an XY plane where the connector 140 is formed. For example, the yaw operating axis 1121 may be formed in a direction parallel to the Z axis as illustrated in FIG. 3, and when the pitch operator 111 rotates, the coordinate system of the yaw operator 112 may relatively change as described above. However, the inventive concept is not limited thereto, and the yaw operating axis 1121 may be formed in various directions by ergonomic design according to the structure of the hand of the user gripping the yaw operator 112.

The yaw operating member 1122 is formed to rotate around the yaw operating axis 1121. For example, when the user holds and rotates the yaw operating member 1122 by the index finger, the yaw operating member 1122 rotates around the yaw operating axis 1121. Then, the resulting rotating force is transmitted to the end tool 120 through the operating force transmitter 130, so that the jaws 121 and 122 of the end tool 120 horizontally rotate in the same direction as the rotation direction of the yaw operating member 1122. To this end, a pulley 1121a may be formed at the yaw operating axis 1121. Also, a yaw wire 130Y may be connected to the pulley 1121a, and the rotating force may be transmitted to the end tool 120 through the operating force transmitter 130 including the yaw wire 130Y, so that the jaws 121 and 122 of the end tool 120 may perform a yaw operation.

The actuation operator 113 includes an actuation operating axis 1131 and an actuation operating member 1132. Herein, the actuation operating axis 1131 may be formed to be at a predetermined angle to the XZ plane where the connector 140 is formed. For example, the actuation operating axis 1131 may be formed in a direction parallel to the Y axis as illustrated in FIG. 2, and when the pitch operator 111 rotates, the coordinate system of the actuation operator 113 may relatively change as described above. However, the inventive concept is not limited thereto, and the actuation operating axis 1131 may be formed in various directions by ergonomic design according to the structure of the hand of the user gripping the actuation operator 113. The actuation operating member 1132 is formed to rotate around the actuation operating axis 1131. For example, when the user holds and rotates the actuation operating member 1132 by the big finger, the actuation operating member 1132 rotates around the actuation operating axis 1131. Then, the resulting rotating force is transmitted to the end tool 120 through the operating force transmitter 130, so that the jaws 121 and 122 of the end tool 120 perform an actuation operation. Herein, as described above, the actuation operation refers to an operation of folding or unfolding the jaws 121 and 122 by rotating the jaws 121 and 122 in opposite directions. That is, when the actuation operator 113 is rotated in one direction, as the first jaw 121 rotates in the counterclockwise direction and the second jaw 122 rotates in the clockwise direction, the end tool 120 is folded; and when the actuation operator 113 is rotated in the opposite direction, as the first jaw 121 rotates in the clockwise direction and the second jaw 122 rotates in the counterclockwise direction, the end tool 120 is unfolded.

A pulley 1131a may be formed at one end portion of the actuation operating axis 1131. An actuation wire 130A may be connected to the pulley 1131a.

Referring to FIG. 3, the pitch operating axis 111 of the pitch operator 111 and the end tool 120 are formed on the same or parallel axis (X axis) in the surgical instrument 100 according to the first embodiment of the present invention.

That is, the pitch operating axis 1111 of the pitch operator 111 is formed at one end portion of the connector 140, and the end tool 120 is formed at the other end portion of the connector 140. Although it is illustrated that the connector 140 is formed to have the shape of a straight line, the inventive concept is not limited thereto. For example, the connector 140 may be curved with a predetermined curvature, or may be bent one or more times. Also in this case, it may be said that the pitch operator 111 and the end tool 120 are formed on substantially the same or parallel axis. Although FIG. 3 illustrates that the pitch operator 111 and the end tool 120 are formed on the same axis (X axis), the inventive concept is not limited thereto. For example, the pitch operator 111 and the end tool 120 may be formed on different axes.

As described above, in the surgical instrument 100 according to the first embodiment of the present invention, the end tool 120 and the operator 110 are formed to extend in the same direction so that the joint operations (e.g., pitch operation and yaw operation) of the end tool 120 and the operator 110 are intuitively identical to each other.

In other words, as illustrated in FIGS. 1E and 1F, as the end tool 120c is formed in front of the end tool rotation center 121c, the operator 110c is also formed in front of the operator rotation center 111c.

Also, since the yaw operator 112 is formed at one end portion of the pitch operator 111, when the pitch operator 111 rotates around the pitch operating axis 1111, the yaw operator 112 also moves around the pitch operating axis 1111 but the end tool 120 also performs a pitch rotation, so that the intuition of the identity between the direction of the yaw operator 112 and the direction of the end tool 120 is not damaged.

That is, even when the extension direction of the yaw operator 112 changes from the +X-axis direction of FIG. 2 by the pitch motion of the pitch operator 111, since the end tool 120 also performs a pitch rotation, the intuition of the identity between the direction of the yaw operator 112 and the direction of the end tool 120 is not damaged.

Thus, although FIG. 2 illustrates the inventive concept that "the operator is formed to extend toward the end tool" in the state of no joint rotation, it may be understood that "the operator is formed to extend toward the end tool" even in the state of a joint rotation in view of the above description.

That is, although the shape of the operator being formed to extend toward the end tool may change according to the operation of another operator, it should be understood in view of the above description, and the shape of the operator being formed to extend toward the end tool may be satisfied in at least any one of various operation states of the operator.

That is, the feature of the operator 110 being formed to extend toward the end tool 120 may also represent that a portion of the operator 110 may become more adjacent to the end tool 120 at least any one moment of the operation with respect to its own joint (i.e., than its own joint).

The operator 110 of the surgical instrument 100 according to the first embodiment of the present invention further includes an operator control member 115 engaged with the pitch operating axis 1111 of the pitch operator 111. Since the operator control member 115 has substantially the same configuration as the end tool control member 123 described later, the relationship between the operator control member 115 and other components of the operator 110 and the end tool control member 123 will be described later.

(Operating Force Transmitter)

Referring to FIGS. 2 to 6, the operating force transmitter 130 of the surgical instrument 100 according to the first embodiment of the present invention includes a yaw wire 130Y, an actuation wire 130A, a pitch wire 130P, a first jaw wire 130J1, a second jaw wire 130J2, and an operating force transmission assembly 135. Herein, the operating force transmission assembly 135 may be accommodated in the pitch operating handle 1112.

First, the operating force transmission assembly 135 of the operating force transmitter 130 will be described below.

As described above, the yaw operator 112 and the actuation operator 113 are formed on one end portion of the pitch operating handle 1112 of the pitch operator 111. Thus, when the pitch operator 111 rotates around the pitch operating axis 1111, the yaw operator 112 and the actuation operator 113 also rotate along with the pitch operator 111. Also, the yaw operator 112 is connected with the first jaw 121 and the second jaw 122 to operate the first jaw 121 and the second jaw 122, and the actuation operator 113 is connected with the first jaw 121 and the second jaw 122 to operate the first jaw 121 and the second jaw 122. However, when the yaw operator 112 is rotated, the first jaw 121 and the second jaw 122 have to rotate in the same direction; and when the actuation operator 113 is rotated, the first jaw 121 and the second jaw 122 have to rotate in opposite directions. In order to implement this operation, a separate structure is required.

Thus, two rotation inputs of the yaw operator 112 and the actuation operator 113 have to be applied to one jaw. Accordingly, a structure for receiving two or more inputs, outputting a rotation of one jaw, and operating differently according to the respective inputs is required. In this case, two rotation inputs have to be independent of each other.

To this end, the surgical instrument 100 according to the first embodiment of the present invention includes an operating force transmission assembly 135 that receives an operating force from the yaw operator 112 and the actuation operator 113 and transmits the operating force to the first jaw 121 and the second jaw 122.

In detail, the operating force transmission assembly 135 includes a yaw pulley 135YP, a yaw operating bar 135B, a first gear 135G1, and a fourth gear 135G4 that are connected with the yaw operator 112 through the yaw wire 130Y to rotate along with the yaw operator 112. Herein, the yaw pulley 135YP, the yaw operating bar 135B, the first gear 135G1, and the fourth gear 135G4 rotate together. Also, it includes a first jaw operating member 135J1 for transmitting an operating force to rotate the first jaw 121 according to the rotation of the yaw operator 112 and the actuation operator 113, and a second jaw operating member 135J2 for transmitting an operating force to rotate the second jaw 122 according to the rotation of the yaw operator 112 and the actuation operator 113. Also, it further includes an actuation gear 135AG rotating along with the actuation operator 113, a second gear 135G2 interposed between the first gear 135G1 and the actuation gear 135AG, and a third gear 135G3 interposed between the actuation gear 135AG and the fourth gear 135G4. In this case, the first gear 135G1, the second gear 135G2, the third gear 135G3, and the fourth gear 135G4 may be sequentially stacked in the Z-axis direction to rotate around a pitch operator center axis 1113. In this case, the actuation gear 135AG rotates around an actuation gear center axis 135AG1 that is fixedly formed in the direction perpendicular to the Z axis. The actuation gear 135AG is connected with the actuation wire 130A to rotate along with the pulley 1131a of the actuation operator 113. This will be described below in more detail.

The first jaw operating member 135J1 includes a first jaw operating gear 135J11, a first jaw connecting member 135J12, a first jaw operating pulley 135J13, and a first jaw operating gear center axis 135J14. The first jaw operating gear 135J11 is interposed in the form of a bevel gear between the third gear 135G3 and the fourth gear 135G4 to revolve around the pitch operator center axis 1113 or rotate around the first jaw operating gear center axis 135J14 according to the relative movement of the third gear 135G3 or the fourth gear 135G4. The first jaw connecting member 135J12 may be formed to connect the first jaw operating gear center axis 135J14 and the first jaw operating pulley 135J13, so that the first jaw operating gear 135J11, the first jaw operating gear center axis 135J14, the first jaw connecting member 135J12, and the first jaw operating pulley 135J13 may rotate together around the pitch operator center axis 1113. The first jaw operating pulley 135J13 may be connected with the first jaw wire 130J1 to transmit the rotation of the yaw operator 112 and the actuation operator 113 to the first jaw 121.

The second jaw operating member 135J2 includes a second jaw operating gear 135J21, a second jaw connecting member 135J22, a second jaw operating pulley 135J23, and a second jaw operating gear center axis 135J24. The second jaw operating gear 135J21 is interposed in the form of a bevel gear between the first gear 135G1 and the second gear 135G2 to revolve around the pitch operator center axis 1113 or rotate around the second jaw operating gear center axis 135J24 according to the relative movement of the first gear 135G1 or the second gear 135G2. The second jaw connecting member 135J22 may be formed to connect the second jaw operating gear center axis 135J24 and the second jaw operating pulley 135J23, so that the second jaw operating gear 135J21, the second jaw operating gear center axis 135J24, the second jaw connecting member 135J22, and the second jaw operating pulley 135J23 may rotate together around the pitch operator center axis 1113. The second jaw operating pulley 135J23 may be connected with the second jaw wire 130J2 to transmit the rotation of the yaw operator 112 and the actuation operator 113 to the second jaw 122.

The operating force transmission assembly 135 may be described below in more detail. The first jaw 121 and the second jaw 122 should rotate with respect to two rotation inputs of the yaw operator 112 and the actuation operator 113, wherein the first jaw 121 and the second jaw 122 should operate differently with respect to the operation of each of the yaw operator 112 and the actuation operator 113. That is, when the yaw operator 112 is rotated, the first jaw 121 and the second jaw 122 should rotate in the same direction; and when the actuation operator 113 is rotated, the first jaw 121 and the second jaw 122 should rotate in opposite directions.

In order to implement this operation, a structure is required to determine the operation of the first jaw 121 with respect to the two rotation inputs of the yaw operator 112 and the actuation operator 113, and the structure includes a first jaw operating gear 135J11, a fourth gear 135G4, and a third gear 135G3 (hereinafter referred to as first differential member).

Also, a structure for determining the operation of the second jaw 122 with respect to the two rotation inputs of the yaw operator 112 and the actuation operator 113 includes a second jaw operating gear 135J21, a first gear 135G1, and a second gear 135G2 (hereinafter referred to as second differential member).

Each of the structures (i.e., the first differential member and the second differential member) includes two input gears and one output gear.

In more detail, the first differential member receives the rotation of the fourth gear 135G4 and the third gear 135G3 and outputs the rotation of the first jaw operating gear 135J11, and the second differential member receives the rotation of the first gear 135G1 and the second gear 135G2 and outputs the rotation of the second jaw operating gear 135J21.

In each operating system, the output gear is rotated according to the rotation input of two input gears, and when the output gear rotates, the entire of the second jaw operating member 135J2 or the jaw operating member (the first jaw operating member 135J1) including the output gear revolves around the pitch operator center axis 1113 in the same direction as one rotation direction of the input gear. Thus, each operating system may receive two inputs to rotate the output gear without affecting another input.

That is, the first differential member may rotate the first jaw 121 according to the rotation input of the yaw operator 112 or the actuation operator 113, and the second differential member may rotate the second jaw 122 according to the rotation of the yaw operator 112 or the actuation operator 113.

In this case, when the yaw operator 112 rotates, the first jaw 121 and the second jaw 122 should rotate in the same direction; and when the actuation operator 113 rotates, the first jaw 121 and the second jaw 122 should rotate in different directions.

Thus, the rotation operation of the yaw operator 112 is configured to rotate one input gear of the second differential member and the first differential member in the same direction, and the rotation operation of the actuation operator 113 is configured to rotate the other input gear of the second differential member and the first differential member in opposite directions.

To this end, the rotation operation of the yaw operator 112 is configured to connect the yaw operating bar 135B to the first gear 135G1 and the fourth gear 135G4 to rotate the first gear 135G1 and the fourth gear 135G4 in the same direction and thus rotate the first jaw operating gear 135J11 and the second jaw operating gear 135J21 in the same direction, so that the first jaw 121 and the second jaw 122 rotate in the same direction to perform a yaw operation.

On the other hand, the rotation operation of the actuation operator 113 is configured to rotate the second gear 135G2 and the third gear 135G3 in opposite directions by the actuation gear 135AG and thus rotate the first jaw operating gear 135J11 and the second jaw operating gear 135J21 in opposite directions, so that the first jaw 121 and the second jaw 122 rotate in opposite directions to perform an actuation operation. Although the present embodiment illustrates the gear as the operating system for extracting one output from two inputs, the inventive concept is not limited thereto and various other operating systems may also be used to extract one output from two inputs.

Although it is illustrated that the first gear 135G1, the second gear 135G2, the third gear 135G3, and the fourth gear 135G4 are sequentially stacked and formed along the pitch operator center axis 1113, the inventive concept is not limited thereto and the above gears may also be formed along the pitch operator center axis 1113 and a separate differential member center axis.

(End Tool)

FIGS. 7 and 8 are perspective views illustrating the end tool of the surgical instrument of FIG. 3, and FIG. 9A is a plan view illustrating the end tool of the surgical instrument of FIG. 3.

Referring to FIGS. 7, 8, and 9A, the end tool 120 according to the first embodiment of the present invention includes an end tool control member 123, and the end tool control member 123 includes a J11 pulley 123J11, a J12 pulley 123J12, a J13 pulley 123J13, a J14 pulley 123J14, and a J15 pulley 123J15 that are related to the rotation motion of the first jaw 121, and a J21 pulley 123J21, a J22 pulley 123J22, a J23 pulley 123J23, a J24 pulley 123J24, and a J25 pulley 123J25 that are related to the rotation motion of the second jaw 122. Herein, the first jaw 121, the J11 pulley 123J11, the J12 pulley 123J12, the J14 pulley 123J14, the second jaw 122, the J21 pulley 123J21, the J22 pulley 123J22, and the J24 pulley 123J24 may be formed to rotate around an end tool pitch operating axis 123PA.

A connector hub 141 may be formed at one end portion of the connector 140 coupled with the end tool 120. The J12 pulley 123J12, the J13 pulley 123J13, the J14 pulley 123J14, the J15 pulley 123J15, the J22 pulley 123J22, the J23 pulley 123J23, the J24 pulley 123J24, and the J25 pulley 123J25 may be coupled to the connector hub 141.

Although it is illustrated that pulleys facing each other are formed to be parallel to each other, the inventive concept is not limited thereto and the pulleys may be formed to have various positions and sizes suitable for the configuration of the end tool.

The J11 pulley 123J11 and the J21 pulley 123J21 are formed to face each other and rotate independently around a jaw rotating axis 123JA. Herein, the first jaw 121 may be coupled to the J11 pulley 123J11 to rotate along with the J11 pulley 123J11, and the second jaw 122 may be coupled to the J21 pulley 123J21 to rotate along with the J21 pulley 123J21. A yaw operation and an actuation operation of the end tool 120 are performed according to the rotations of the J11 pulley 123J11 and the J21 pulley 123J21. That is, the yaw operation is performed when the J11 pulley 123J11 and the J21 pulley 123J21 rotate in the same direction, and the actuation operation is performed when the J11 pulley 123J11 and the J21 pulley 123J21 rotate in opposite directions.

A J16 pulley 123J16 and a J26 pulley 123J26 may be additionally provided as additional pulleys on one side of the J11 pulley 123J11 and the J21 pulley 123J21, and the additional pulleys may be formed to rotate around an additional pulley axis 123S. Although it is illustrated that the J16 pulley 123J16 and the J26 pulley 123J26 are formed to rotate around one additional pulley axis 123S, each of the additional pulleys may also be formed to rotate around a separate axis. In other words, as the additional pulley, the J16 pulley 123J16 may be disposed between the J11 pulley 123J11 and the J12 pulley 123J12/the J14 pulley 123J14. Also, as the additional pulley, the J26 pulley 123J26 may be disposed between the J21 pulley 123J21 and the J22 pulley 123J22/the J24 pulley 123J24. The additional pulleys will be described later in more detail.

The elements related to the rotation of the J11 pulley 123J11 will be described below.

On one side of the J11 pulley 123J11, the J12 pulley 123J12 and the J14 pulley 123J14 are disposed to face each other. Herein, the J12 pulley 123J12 and the J14 pulley 123J14 are formed to rotate independently around the Y-axis direction. Also, on one side of the J12 pulley 123J12 and the J14 pulley 123J14, the J13 pulley 123J13 and the J15 pulley 123J15 are disposed to face each other. Herein, the J13 pulley 123J13 and the J15 pulley 123J15 are formed to rotate independently around the Y-axis direction. Although it is illustrated that all of the J12 pulley 123J12, the J13 pulley 123J13, the J14 pulley 123J14, and the J15 pulley 123J15 are formed to rotate around the Y-axis direction, the present invention is not limited thereto, and the rotating axes of the respective pulleys may be formed in various directions according to their configurations.

The first jaw operating wire 130J1 may be wound to at least partially contact the J13 pulley 123J13, the J12 pulley 123J12, the J11 pulley 123J11, the J16 pulley 123J16, the J14 pulley 123J14, and the J15 pulley 123J15, and the first jaw operating wire 130J1 may move along the above pulleys while rotating the above pulleys.

Thus, when the first jaw operating wire 130J1 is pulled in the direction of an arrow J1R of FIG. 9A, the first jaw operating wire 130J1 rotates the J15 pulley 123J15, the J14 pulley 123J14, the J16 pulley 123J16, the J11 pulley 123J11, the J12 pulley 123J12, and the J13 pulley 123J13. In this case, the J11 pulley 123J11 rotates in the direction of an arrow R of FIG. 9A to rotate the first jaw 121 together.

On the other hand, when the first jaw operating wire 130J1 is pulled in the direction of an arrow J1L of FIG. 9A, the first jaw operating wire 130J1 rotates the J13 pulley 123J13, the J12 pulley 123J12, the J11 pulley 123J11, the J16 pulley 123J16, the J14 pulley 123J14, and the J15 pulley 123J15. In this case, the J11 pulley 123J11 rotates in the direction of an arrow L of FIG. 9A to rotate the first jaw 121 together.

The additional pulleys 123J16 and 123J26 will be described below in more detail.

The additional pulleys 123J16 and 123J26 may contact the first jaw wire 130J1 and the second jaw wire 130J2 to change the disposition path of the first jaw wire 130J1 and the second jaw wire 130J2 by some degree, thereby expanding the rotation radius of the first jaw 121 and the second jaw 122. That is, when an additional pulley is not disposed as illustrated in FIG. 9B, a first jaw 121' and a second jaw 122' may rotate only up to a right angle; however, in an embodiment of the present invention, the additional pulleys 123J16 and 123J26 may be additionally provided to increase the maximum rotation angle by 0 as illustrated in FIG. 9A. This will be described below in more detail.

Referring to FIG. 9B, since a first jaw wire 130J1' is fixedly coupled to a J11 pulley 123J11' and a second jaw wire 130J2' is fixedly coupled to a J21 pulley (not illustrated), when an additional pulley is not disposed, the J11 pulley 123J11' and the J21 pulley (not illustrated) may rotate only up to a line M of FIG. 9B. In other words, a coupler of the first jaw wire 130J1' and the J11 pulley 123J11' may rotate only up to the tangential direction of the first jaw wire 130J11'. In this case, when the first jaw 121' and the second jaw 122' performs an actuation operation while being located at the line M of FIG. 9B, the one jaw may be unfolded but the other jaw may not be unfolded because it may not rotate above the line M. Thus, while the first jaw 121' and the second jaw 122' is performing a yaw operation by some degree or more, an actuation operation may not be smoothly performed.

In order to solve this problem, in the surgical instrument 100 according to an embodiment of the present invention, the J16 pulley 123J16 and the J26 pulley 123J26 are additionally disposed as additional pulleys on one side of the J11 pulley 123J11 and the J21 pulley 123J21. In this manner, the J16 pulley 123J16 and the J26 pulley 123J26 may be disposed to change the disposition path of the first jaw wire 130J1 and the second jaw wire 130J2 by some degree and thereby change the tangential direction of the first jaw wire 130J1 and the second jaw wire 130J2, so that a coupler of the first jaw wire 130J1 and the J11 pulley 123J11 and a coupler of the second jaw wire 130J2 and the J21 pulley 123J21 may rotate up to a line N of FIG. 9A. That is, the coupler of the first jaw wire 130J1 and the J11 pulley 123J11 may rotate until it is located on the internal common tangent of the J11 pulley 123J11 and the J16 pulley 123J16 Likewise, the coupler of the second jaw wire 130J2 and the J21 pulley 123J21 may rotate until it is located on the internal common tangent of the J21 pulley 123J21 and the J26 pulley 123J26.

In this manner, according to the present invention, the rotation radius of the first jaw 121 and the second jaw 122 may be expanded to expand the operation range of the normal opening/closing actuation operation.

The elements related to the rotation of the J21 pulley 123J21 will be described below.

On one side of the J21 pulley 123J21, the J22 pulley 123J22 and the J24 pulley 123J24 are disposed to face each other. Herein, the J22 pulley 123J22 and the J24 pulley 123J24 are formed to rotate independently around the Y-axis direction. Also, on one side of the J22 pulley 123J22 and the J24 pulley 123J24, the J23 pulley 123J23 and the J25 pulley 123J25 are disposed to face each other. Herein, the J23 pulley 123J23 and the J25 pulley 123J25 are formed to rotate independently around the Y-axis direction. Although it is illustrated that all of the J22 pulley 123J22, the J23 pulley 123J23, the J24 pulley 123J24, and the J25 pulley 123J25 are formed to rotate around the Y-axis direction, the present invention is not limited thereto, and the rotating axes of the respective pulleys may be formed in various directions according to their configurations.

The second jaw operating wire 130J2 may be wound to at least partially contact the J23 pulley 123J23, the J22 pulley 123J22, the J21 pulley 123J21, the J26 pulley 123J26, the J24 pulley 123J24, and the J25 pulley 123J25, so that the second jaw operating wire 130J2 may move along the above pulleys while rotating the above pulleys.

Thus, when the second jaw operating wire 130J2 is pulled in the direction of an arrow J2R of FIG. 9A, the second jaw operating wire 130J2 rotates the J25 pulley 123J25, the J24 pulley 123J24, the J21 pulley 123J21, the J26 pulley 123J26, the J22 pulley 123J22, and the J23 pulley 123J23. In this case, the J21 pulley 123J21 rotates in the direction of an arrow R of FIG. 9A to rotate the second jaw 122 together.

On the other hand, when the second jaw operating wire 130J2 is pulled in the direction of an arrow J2L of FIG. 9A, the second jaw operating wire 130J2 rotates the J23 pulley 123J23, the J22 pulley 123J22, the J21 pulley 123J21, the J26 pulley 123J26, the J24 pulley 123J24, and the J25 pulley 123J25. In this case, the J21 pulley 123J21 rotates in the direction of an arrow L of FIG. 9A to rotate the second jaw 122 together.

When one end portion of the first jaw operating wire 130J1 is pulled in the direction of the arrow J1R of FIG. 9A and the other end portion of the first jaw operating wire 130J1 is pulled in the direction of the arrow J1L of FIG. 9A (that is, when both end portions of the first jaw operating wire 130J1 are pulled), an end tool hub 123a and the first jaw 121 and the second jaw 122 coupled thereto rotate around the end tool pitch operating axis 123PA in the counterclockwise direction, so that the end tool 120 rotates downward to perform a pitch motion.

On the other hand, when one end portion of the second jaw operating wire 130J2 is pulled in the direction of the arrow J2R of FIG. 9A and the other end portion of the second jaw operating wire 130J2 is pulled in the direction of the arrow J2L of FIG. 9A, the end tool hub 123a and the first jaw 121 and the second jaw 122 coupled thereto rotate around the end tool pitch operating axis 123PA in the clockwise direction, so that the end tool 120 rotates upward to perform a pitch motion.

The end tool 120 of the surgical instrument 100b according to the present invention further includes a pitch pulley 123P, the operator 110 (see FIG. 11) further includes a pitch pulley 115P (see FIG. 11), and the operating force transmitter 130 further includes a pitch wire 130P. In detail, the pitch pulley 123P of the end tool 120 may be fixedly coupled with the end tool hub 123a to rotate around the end tool pitch operating axis 123PA along with the end tool hub 123a. The pitch pulley 115P of the operator 110 may be fixedly connected with an operator hub 115a to rotate around the pitch operating axis 1111 along with the operator hub 115a. Also, the pitch wire 130P may connect the pitch pulley 123P of the end tool 120 and the pitch pulley 115P of the operator 110.

Thus, when the user grips the pitch operating handle 1112 of the pitch operator 111 and rotates the pitch operating handle 1112 around the pitch operating axis 1111, the operator hub 115a connected with the pitch operating handle 1112 and the pitch pulley 115P connected therewith rotate around the pitch operating axis 1111, the rotation of the pitch pulley 115P is transmitted to the pitch pulley 123P of the end tool 120 through the pitch wire 130P, and the pitch pulley 123P also rotates together. Consequently, the end tool 120 rotates to perform a pitch motion.

That is, the surgical instrument 100 according to the first embodiment of the present invention includes the pitch pulley 123P of the end tool 120, the pitch pulley 115P of the operator 110, and the pitch wire 130P of the operating force transmitter 130 to more perfectly transmit the operating force of the pitch operation of the pitch operator 111 to the end tool 120, thereby improving the operational reliability.

(Pitch Operation Control and Wire Minoring)

FIG. 10 is a schematic view illustrating a pitch operation of the surgical instrument of FIG. 3, and FIG. 11 is a perspective view illustrating a pitch operation of the surgical instrument of FIG. 3.

As described above, the operator 110 of the surgical instrument 100 according to the first embodiment of the present invention further includes an operator control member 115 connected with the pitch operating axis 1111 of the pitch operator 111. The operator control member 115 has substantially the same configuration of the end tool control member 123, and the end tool control member 123 and the operator control member 115 are disposed symmetrical to each other with respect to the YZ plane of FIG. 3. In other words, it may be said that the end tool control member 123 and the operator control member 115 are mirrored with respect to the YZ plane of FIG. 3.

In detail, the operator control member 115 includes a J11 pulley 135J13, a J12 pulley 115J12, a J13 pulley 115J13, a J14 pulley 115J14, and a J15 pulley 115J15 that are related to the rotation motion of the first jaw 121, and a J21 pulley 135J23, a J22 pulley 115J22, a J23 pulley 115J23, a J24 pulley 115J24, and a J25 pulley 115J25 that are related to the rotation motion of the second jaw 122.

The first jaw operating wire 130J1 may be wound to at least partially contact the J13 pulley 115J13, the J12 pulley 115J12, the J11 pulley 135J13, the J14 pulley 115J14, and the J15 pulley 115J15 of the operator control member 115, and the first jaw operating wire 130J1 may move along the above pulleys while rotating the above pulleys.

The second jaw operating wire 130J2 may be wound to at least partially contact the J23 pulley 115J23, the J22 pulley 115J22, the J21 pulley 135J23, the J24 pulley 115J24, and the J25 pulley 115J25 of the operator control member 115, and the second jaw operating wire 130J2 may move along the above pulleys while rotating the above pulleys.

Herein, the rotating axis of the J12 pulley 115J12, the J14 pulley 115J14, the J22 pulley 115J22, and the J24 pulley 115J24 may be identical to the pitch operating axis 1111 of the pitch operator 111. Also, a portion extending from the rotating axis of the J11 pulley 135J13 and the J21 pulley 135J23 may be identical to the pitch operating handle 1112 of the pitch operator 111.

The pitch operation in the first embodiment of the present invention is performed as follows:

When the user grips the pitch operating handle 1112 (see FIG. 2) of the pitch operator 111 of the operator 110 and rotates the pitch operating handle 1112 around the pitch operating axis 1111 in the direction of an arrow OP (Operator Pitch) of FIG. 10, the first jaw operating wire 130J1 is pulled toward the operator 110 and moves in the direction of an arrow PJ1 of FIG. 10. At the same time, the second jaw operating wire 130J2 is unwound from the operator 110, moves toward the end tool 120, and moves in the direction of an arrow PJ2 of FIG. 10. Then, as the first jaw operating wire 130J1 is pulled toward the operator 110, the J12 pulley 123J12 and the J14 pulley 123J14 rotate around the end tool pitch rotating axis 123PA in the counterclockwise direction. At the same time, as the second jaw operating wire 130J2 is pulled toward the end tool 120, the J22 pulley 123J22 and the J24 pulley 123J24 rotate around the end tool pitch rotating axis 123PA in the counterclockwise direction. Consequently, the end tool hub 123a and the first jaw 121 and the second jaw 122 coupled therewith rotate downward to perform a pitch motion.

In this manner, since the end tool control member 123 and the operator control member 115 are disposed symmetrical to each other (i.e., mirrored) with respect to the YZ plane of FIG. 3, the pitch operation may be conveniently performed. That is, the pitch operation may be performed regardless of the yaw operation and the actuation operation. Herein, the yaw operation refers to an operation in which the J11 pulley 135J13 and the J21 pulley 135J23 of the operator control member 115 rotate around the pitch operator center axis 1113 and thus the J11 pulley 123J11 and the J21 pulley 123J21 of the end tool control member 123 rotate around the jaw rotating axis 123JA to rotate the jaws 121 and 122.

(Overall Operation of First Embodiment)

Hereinafter, an overall configuration for the pitch operation, the yaw operation, and the actuation operation of the surgical instrument 100 according to the first embodiment of the present invention will be summarized with reference to the above descriptions.

For the configuration of the end tool 120 of the present embodiment, the operating force transmitter 130 capable of dividing the operation input of the operator 110 into a pitch operation, a yaw operation, and an actuation operation is necessary to perform the pitch, yaw, and actuation operations of the end tool 120. As described above, through the structure in which the end tool control member 123 and the operator control member 115 are disposed symmetrical to each other, the rotation operation of the pitch operator 111 enables the pitch operation of the end tool 120 regardless of the operations of the yaw operator 112 and the actuation operator 113. Also, the operating force transmission assembly 135 is provided to convert the operation of the yaw operator 112 and the actuation operator 113 into the operation of two jaws of the end tool 120, thereby connecting the operation of the yaw operator 112 and the actuation operator 113 to the yaw operation and the actuation operation of the end tool 120. That is, by the operating force transmission assembly 135, the rotation of the yaw operator 112 causes the two jaws to rotate in the same direction, and the rotation of the actuation operator 113 causes the two jaws to rotate in different directions.

This will be described below in more detail.

First, the pitch operation will be described below.

As described above, when the user grips the pitch operating handle 1112 of the pitch operator 111 of the operator 110 and rotates the pitch operating handle 1112 around the pitch operating axis 1111 in the direction of the arrow OP of FIG. 10, the operator control member 115 also rotates around the pitch operating axis 1111. Then, the first jaw operating wire 130J1 wound around the operation control member 115 is pulled toward the operator 110 and moves in the direction of the arrow PJ1 of FIG. 10. At the same time, the second jaw operating wire 130J2 wound around the operation control member 115 is unwound from the operator control member 115 and moves in the direction of the arrow PJ2 of FIG. 10. Then, the end tool control member 123 connected with the first jaw operating wire 130J1 and the second jaw operating wire 130J2 rotates around the end tool pitch operating axis 1231 in the direction of an arrow EP of FIG. 10 to perform a pitch motion.

The yaw operation will be described below. FIGS. 12 and 13 are views illustrating a yaw operation of the surgical instrument of FIG. 3.

Referring to FIGS. 5, 6, 12, and 13, when the yaw operator 112 rotates in the direction of an arrow Y of FIG. 13, the pulley 1121a of the yaw operator 112 and the yaw pulley 135YP connected thereto through the yaw wire 130Y rotate around the respective axes. Also, when the yaw pulley 135YP rotates, the first gear 135G1 and the fourth gear 135G4 rotate around the pitch operator center axis 1113 through the yaw operating bar 135B.

Then, when the first gear 135G1 and the fourth gear 135G4 rotate around the pitch operator center axis 1113, the first gear 135G1 rotates in the direction of the arrow Y with respect to the second gear 135G2, the second jaw operating gear 135J21 formed at the second jaw operating member 135J2 rotates in the direction C with respect to the second jaw operating gear center axis 135J24, and the entire of the second jaw operating member 135J2 also rotates around the pitch operator center axis 1113 in the direction of the arrow Y.

Also, the fourth gear 135G4 rotates in the direction Y because it is integrally connected with the first gear 135G1. In this case, the first jaw operating gear 135J11 formed at the first jaw operating member 135J1 rotates in the direction B with respect to the first jaw operating gear center axis 135J14, and the entire of the first jaw operating member 135J1 also rotates around the pitch operator center axis 1113 in the direction Y.

Thus, the first jaw operating member 135J1 and the second jaw operating member 135J2 rotate in the same direction, and the first jaw 121 connected to the first jaw operating member 135J1 through the first jaw wire 130J1 and the second jaw 122 connected to the second jaw operating member 135J2 through the second jaw wire 130J2 rotate in the same direction to perform a yaw operation.

The actuation operation will be described below. FIGS. 14 and 15 are views illustrating an actuation operation of the surgical instrument of FIG. 3.

Referring to FIGS. 5, 6, 14, and 15, when the actuation operator 113 rotates in the direction of an arrow A of FIG. 15, the pulley 1131a of the actuation operator 113 and the actuation gear 135AG connected thereto through the actuation wire 130A rotate around the respective axes in the direction of the arrow A.

In this manner, when the actuation gear 135AG rotates around the actuation gear center axis 135AG1, the second gear 135G2 engaged with the upper side of the actuation gear 135AG rotates in the direction J2 of FIG. 15, the second jaw operating gear 135J21 engaged between the first gear 135G1 and the second gear 135G2 rotates in the direction E with respect to the second jaw operating gear center axis 135J24, and the entire of the second jaw operating member 135J2 also rotates around the pitch operator center axis 1113 in the direction of an arrow J2.

Also, when the actuation gear 135AG rotates around the actuation gear center axis 135AG1, the third gear 135G3 engaged with the lower side of the actuation gear 135AG rotates in the direction J1 of FIG. 15, the first jaw operating gear 135J11 engaged between the third gear 135G3 and the fourth gear 135G4 rotates in the direction F with respect to the first jaw operating gear center axis 135J14, and the entire of the first jaw operating member 135J1 also rotates around the pitch operator center axis 1113 in the direction of an arrow J1.

Thus, the first jaw 121 connected to the first jaw operating member 135J1 through the first jaw wire 130J1 and the second jaw 122 connected to the second jaw operating member 135J2 through the second jaw wire 130J2 rotate in opposite directions to perform an actuation motion for unfolding the two jaws.

In this manner, according to the present invention, a surgical instrument performing an output operation of an end tool by the independent inputs of a pitch operating member, a yaw operating member, and an actuation operating member may be implemented solely by a mechanical configuration without using motors, electronic control, or software. That is, since the pitch operation, the yaw operation, and the actuation operation, which affect each other, are separated from each other solely by mechanism, the configuration of the surgical instrument may be significantly simplified.

Also, the rotating force of the operator 110 may be transmitted to the end tool 120 solely by the minimum gear, wire, and pulley structure. In particular, according to the present invention, since the operation direction of the operator 110 is intuitively identical to the operation direction of the end tool 120, the convenience of a surgical operator may be improved and the accuracy of a surgical operation may be improved. Furthermore, since the end tool control member 123 and the operator control member 115 are disposed symmetrical to each other (i.e., mirrored) with respect to the YZ plane of FIG. 10, the pitch operation may be conveniently performed. That is, the pitch operation may be performed regardless of the yaw operation and the actuation operation.

MODE OF THE INVENTION

Second Embodiment of Surgical Instrument

Hereinafter, a surgical instrument 200 according to a second embodiment of the present invention will be described. The surgical instrument 200 according to the second embodiment of the present invention is different in terms the configuration of an operating force transmission assembly 235 from the surgical instrument 100 (see FIG. 2) according to the first embodiment of the present invention.

This difference in the configuration from the first embodiment will be described later in detail.

FIG. 16 is a perspective view of a surgical instrument according to a second embodiment of the present invention, FIG. 17 is a plan view of the surgical instrument of FIG. 16, and FIG. 18 is a perspective view illustrating an operator of the surgical instrument of FIG. 16.

Referring to FIGS. 16, 17, and 18, the surgical instrument 200 according to the second embodiment of the present invention includes an operator 210, an end tool 220, an operating force transmitter 230, and a connector 240.

The operator 210 includes a pitch operator 211 controlling a pitch motion of the end tool 220, a yaw operator 212 controlling a yaw motion of the end tool 220, and an actuation operator 213 controlling an actuation motion of the end tool 220.

The pitch operator 211 includes a pitch operating axis 2111 and a pitch operating handle (not illustrated). The yaw operator 212 includes a yaw operating axis 2121 and a yaw operating member 2122. The actuation operator 213 includes an actuation operating axis 2131 and an actuation operating member 2132.

The operating force transmitter 230 includes a yaw wire 230Y, an actuation wire 230A, a pitch wire (not illustrated), a first jaw wire 230J1, a second jaw wire 230J2, and an operating force transmission assembly 235. Herein, the operating force transmission assembly 235 may be accommodated in the pitch operating handle 2112.

First, the operating force transmission assembly 235 of the operating force transmitter 230 will be described below. The operating force transmission assembly 235 receives the operating force of the yaw operator 212 and the actuation operator 213 and transmits the received operating force to a first jaw 221 and a second jaw 222.

In detail, the operating force transmission assembly 235 includes a yaw pulley 235YP, a first gear 235G1, and a fourth gear 235G4 that are connected with the yaw operator 212 through the yaw wire 230Y to rotate along with the yaw operator 212. Herein, the yaw pulley 235YP, the first gear 235G1, and the fourth gear 235G4 rotate together by being connected to each other by a yaw operating bar 235B. Also, it includes a first jaw operating member 235J1 for transmitting an operating force to rotate the first jaw 221 according to the rotation of the yaw operator 212 and the actuation operator 213, and a second jaw operating member 235J2 for transmitting an operating force to rotate the second jaw 222 according to the rotation of the yaw operator 212 and the actuation operator 213. Also, it further includes an actuation gear 235AG rotating along with the actuation operator 213, a second gear 235G2 interposed between the first gear 235G1 and the actuation gear 235AG, and a third gear 235G3 interposed between the actuation gear 235AG and the fourth gear 235G4. In this case, the first gear 235G1, the second gear 235G2, the third gear 235G3, and the fourth gear 235G4 may be sequentially stacked and formed in the direction of a pitch operator center axis 2113 to rotate around the pitch operator center axis 2113. Herein, the actuation gear 235AG rotates around an actuation gear center axis 235AG1 that is fixedly formed in the direction perpendicular to the Z axis. The actuation gear 235AG is connected with the actuation wire 230A to rotate along with the pulley 2131a of the actuation operator 213. This will be described below in more detail.

The first jaw operating member 235J1 includes a first jaw operating gear 235J11, a first jaw connecting member 235J12, a first jaw operating pulley 235J13, and a first jaw operating gear center axis 235J14. The first jaw operating gear 235J11 is interposed in the form of a bevel gear between the first gear 235G1 and the second gear 235G2 to revolve around the pitch operator center axis 2113 or rotate around the first jaw operating gear center axis 235J14 according to the relative movement of the first gear 235G1 or the second gear 235G2. The first jaw connecting member 235J12 may be formed to connect the first jaw operating gear center axis 235J14 and the first jaw operating pulley 235J13, so that the first jaw operating gear 235J11, the first jaw operating gear center axis 235J14, the first jaw connecting member 235J12, and the first jaw operating pulley 235J13 may rotate together around the pitch operator center axis 2113. The first jaw operating pulley 235J13 may be connected with the first jaw wire 230J1 to transmit the rotation of the yaw operator 212 and the actuation operator 213 to the first jaw 221.

Herein, the first jaw connecting member 235J12 may be formed to connect to the pitch operator center axis 2113 and may be formed in the shape of bars extending respectively in different directions from the pitch operator center axis 2113, one of the bars may be formed to connect with the first jaw operating gear 235J11, and the other bar may be formed to connect with the first jaw operating pulley 235J13. In this case, the bar connected with the first jaw operating pulley 235J13 may be formed to be more distant from the pitch operator center axis 2113 than the second jaw connecting member 235J22. Thus, the first jaw connecting member 235J12 and the second jaw connecting member 235J22 may not collide with each other. That is, since the bar connected with the first jaw operating pulley 235J13 is formed to be distant from the pitch operator center axis 2113, the first jaw operating member 235J1 and the second jaw operating member 235J2 may rotate freely without interfering with each other.

The second jaw operating member 235J2 includes a second jaw operating gear 235J21, a second jaw connecting member 235J22, a second jaw operating pulley 235J23, and a second jaw operating gear center axis 235J24. The second jaw operating gear 235J21 is interposed in the form of a bevel gear between the first gear 235G1 and the second gear 235G2 to revolve around the pitch operator center axis 2113 or rotate around the second jaw operating gear center axis 235J24 according to the relative movement of the third gear 235G3 or the fourth gear 235G4.

The second jaw connecting member 235J22 may be formed to connect the second jaw operating gear center axis 235J24 and the second jaw operating pulley 235J23, so that the second jaw operating gear 235J21, the second jaw operating gear center axis 235J24, the second jaw connecting member 235J22, and the second jaw operating pulley 235J23 may rotate together around the pitch operator center axis 2113. The second jaw operating pulley 235J23 may be connected with the second jaw wire 230J2 to transmit the rotation of the yaw operator 212 and the actuation operator 213 to the second jaw 222.

Although the present invention has been described with reference to the embodiments illustrated in the drawings, this is merely an example and those of ordinary skill in the art will understand that various modifications may be made therein. Thus, the spirit and scope of the present invention should be defined by the appended claims.

INDUSTRIAL APPLICABILITY

The present invention may be applied to surgical instruments that may be manually operated to perform laparoscopic operations or various surgical operations.

The invention claimed is:

1. A surgical instrument comprising:
an end tool comprising a first jaw and a second jaw configured to rotate independently;
an operator comprising a pitch operator controlling a pitch motion of the end tool, a yaw operator controlling a yaw motion of the end tool, and an actuation operator controlling an actuation motion of the end tool;
an operating force transmitter comprising a first jaw wire connected with the first jaw to transmit an operation of the operator to the first jaw, a second jaw wire connected with the second jaw to transmit an operation of the operator to the second jaw, and one or more differential members configured to transmit a rotation of the yaw operator or the actuation operator to the first jaw or the second jaw via the first jaw wire or the second jaw wire;
a connector configured to extend in a first direction and having one end portion coupled to the end tool and the other end portion coupled to the operator to connect the operator and the end tool;
a first jaw operating member; and
a second jaw operating member,
wherein the operating force transmitter comprises:
a first gear, a second gear, a third gear, and a fourth gear formed sequentially along a differential member center axis; and
an actuation gear configured to engage independently with the second gear and the third gear and configured to rotate around an actuation gear center axis according to the rotation of the actuation operator,
wherein the first jaw operating member comprises:
a first jaw operating gear configured to engage independently with the third gear and the fourth gear and configured to rotate around a first jaw operating gear center axis;
a first jaw operating pulley connected with the first jaw wire to rotate along with the first jaw wire; and
a first jaw connecting member connecting the first jaw operating gear and the first jaw operating pulley, and
wherein the second jaw operating member comprises:
a second jaw operating gear configured to engage independently with the first gear and the second gear and configured to rotate around a second jaw operating gear center axis;
a second jaw operating pulley connected with the second jaw wire to rotate along with the second jaw wire; and
a second jaw connectinq member connectinq the second jaw operating gear and the second jaw operating pulley.

2. The surgical instrument of claim 1, wherein at least a portion of the operator is configured to be more adjacent to the end tool than a rotating axis of the operator in one or more operation states where the operator is rotated by a predetermined angle around a second direction for a pitch operation.

3. The surgical instrument of claim 1, wherein the yaw operator or the actuation operator is formed at one end portion of the pitch operator.

4. The surgical instrument of claim 3, wherein the yaw operator or the actuation operator rotates along with the pitch operator according to a rotation of the pitch operator.

5. The surgical instrument of claim 1, wherein the one or more differential members comprises:
a first differential member comprising a first input unit connected to the yaw operator, a second input unit connected to the actuation operator, and an output unit connected to the first input unit and the second input unit; and
a second differential member comprising a first input unit connected to the yaw operator, a second input unit connected to the actuation operator, and an output unit connected to the first input unit and the second input unit,
wherein
the yaw operator is connected to the first input unit of the first differential member and the first input unit of the second differential member;
an operation of the yaw operator is configured to rotate the first input unit of the first differential member and the output unit of the first differential member connected thereto and the first input unit of the second differential member and the output unit of the second differential member connected thereto in an identical direction;
the actuation operator is connected to the second input unit of the first differential member and the second input unit of the second differential member; and
an operation of the actuation operator is configured to rotate the second input unit of the first differential member and the output unit of the first differential member connected thereto and the second input unit of the second differential member and the output unit of the second differential member connected thereto in opposite directions, independently.

6. The surgical instrument of claim 5, wherein
the output unit of the first differential member is connected with the first jaw;
the output unit of the second differential member is connected with the second jaw; and
the first jaw or the second jaw is configured to move according to the operation of the yaw operator or the actuation operator.

7. The surgical instrument of claim 1, wherein
the pitch operator is configured to rotate around a second direction perpendicular to the first direction,
the operator is configured to have a plurality of operation states,
at least a portion of the pitch operator is configured to be more adjacent to the end tool than a pitch operating axis in at least any one operation state of the pitch operator,
at least a portion of the yaw operator is configured to be more adjacent to the end tool than a yaw operating axis in at least any one operation state of the yaw operator.

8. The surgical instrument of claim 1, wherein the first gear and the fourth gear are configured to rotate in the same direction according to the rotation of the yaw operator.

9. The surgical instrument of claim 1, wherein the second gear and the third gear rotate in opposite directions when the actuation gear rotates around the actuation gear center axis.

10. The surgical instrument of claim 1, wherein
the first jaw operating gear is interposed in the form of a bevel gear between the third gear and the fourth gear to revolve around the differential member center axis or rotate around the first jaw operating gear center axis according to a relative movement of the third gear or the fourth gear; and
the second jaw operating gear is interposed in the form of a bevel gear between the first gear and the second gear to revolve around the differential member center axis or rotate around the second jaw operating gear center axis according to a relative movement of the first gear or the second gear.

11. The surgical instrument of claim 10, wherein
the first jaw operating member and the second jaw operating member rotate in the same direction when the yaw operator rotates; and
the first jaw operating member and the second jaw operating member rotate in opposite directions when the actuation operator rotates.

12. The surgical instrument of claim 1, wherein the first jaw connecting member is configured to be inserted into the differential member center axis and is formed in the shape of bars extending respectively in different directions from the differential member center axis, one of the bars is configured to connect with the first jaw operating gear, and the other bar is configured to connect with the first jaw operating pulley.

13. The surgical instrument of claim 12, wherein the other bar connecting with the first jaw operating pulley is configured to be more distant from the differential member center axis than the second jaw connecting member.

* * * * *